(12) United States Patent
Lue

(10) Patent No.: US 11,083,746 B2
(45) Date of Patent: *Aug. 10, 2021

(54) USE OF IMMOBILIZATION PARTICLES FOR REMOVAL OF MICROORGANISMS AND/OR CHEMICALS

(71) Applicant: NuBiome, Inc., Mountain View, CA (US)

(72) Inventor: Brian C. Lue, Mountain View, CA (US)

(73) Assignee: NuBiome, Inc., Mountain View, CA (US)

( * ) Notice: Subject to any disclaimer, the term of this patent is extended or adjusted under 35 U.S.C. 154(b) by 195 days.

This patent is subject to a terminal disclaimer.

(21) Appl. No.: 16/369,714

(22) Filed: Mar. 29, 2019

(65) Prior Publication Data
US 2019/0224227 A1   Jul. 25, 2019

Related U.S. Application Data

(63) Continuation of application No. 15/002,300, filed on Jan. 20, 2016, now Pat. No. 10,245,279, which is a continuation of application No. 13/344,315, filed on Jan. 5, 2012, now abandoned, which is a continuation-in-part of application No. 12/660,459, filed on Feb. 26, 2010, now abandoned.

(60) Provisional application No. 61/208,629, filed on Feb. 26, 2009, provisional application No. 61/212,375, filed on Apr. 11, 2009.

(51) Int. Cl.
| | |
|---|---|
| *A61K 31/713* | (2006.01) |
| *A61K 9/48* | (2006.01) |
| *A61K 9/02* | (2006.01) |
| *A61K 9/06* | (2006.01) |
| *A61K 9/70* | (2006.01) |
| *C12Q 1/24* | (2006.01) |
| *G01N 33/569* | (2006.01) |
| *C07K 16/08* | (2006.01) |
| *C07K 16/12* | (2006.01) |
| *C07K 16/14* | (2006.01) |
| *A61K 9/00* | (2006.01) |

(52) U.S. Cl.
CPC .......... *A61K 31/713* (2013.01); *A61K 9/0031* (2013.01); *A61K 9/0053* (2013.01); *A61K 9/02* (2013.01); *A61K 9/06* (2013.01); *A61K 9/4841* (2013.01); *A61K 9/7007* (2013.01); *C07K 16/08* (2013.01); *C07K 16/12* (2013.01); *C07K 16/14* (2013.01); *C12Q 1/24* (2013.01); *G01N 33/569* (2013.01)

(58) Field of Classification Search
CPC .. A61K 31/713; A61K 9/0031; A61K 9/0053; A61K 9/02; A61K 9/06; A61K 9/4841; A61K 9/7007; C07K 16/08; C07K 16/12; C07K 16/14; C12Q 1/24; G01N 33/569
See application file for complete search history.

(56) References Cited

U.S. PATENT DOCUMENTS

| | | | |
|---|---|---|---|
| 4,514,508 A | 4/1985 | Hirschfeld | |
| 7,195,872 B2 | 3/2007 | Agrawal et al. | |
| 10,245,279 B2 * | 4/2019 | Lue ...................... | A61K 9/4841 |
| 2003/0031671 A1 | 2/2003 | Welt et al. | |
| 2003/0148401 A1 | 8/2003 | Agrawal et al. | |
| 2007/0148044 A1 | 6/2007 | Murata | |
| 2010/0256343 A1 | 10/2010 | Lue | |
| 2012/0108787 A1 | 5/2012 | Lue | |

FOREIGN PATENT DOCUMENTS

| | | |
|---|---|---|
| EP | 1614460 | 11/2006 |
| WO | WO2007/149042 | 12/2007 |

OTHER PUBLICATIONS

Shapira, R, et al. 1971. Biological activity and synthesis of an encephalitogenic determinant. Science 172: 736-738.
Westall, F.C, et al. 1977. Hyperacute autoimmune encephalomyelitis-unique determinant conferred by serine in a synthetic autoantigen. Nature 269: 425-427.
Dua, H.S., et al. 1991. Structure-function studies of s-antigen: use of proteases to reveal a dominant uveitogenic site. Autoimmunity 10: 153-163.
Yoshikawa, H., et al. 1997. A 17-mer self-peptide of acetylcholine receptor binds to B cell MHC class II, activates helper T cells, and stimulates autoantibody production and electrophysiologic signs of myasthenia gravis. J. lmmunol. 159: 1570-1577.
Bellone, M., et al. 1989. The main region of the nicotinic acetylcholine receptor. J. Immunol. 143: 3568-3579.
James, J.A., et al. 1999. Side-chain specificities and molecular modeling of peptide determinants for two anti-Sm B/B' autoantibodies. J. Autoimmunity 12: 43-49.
Vera, C., et al. 2000. Tropmodulin-binding site mapped to residues 7-14 at the N-terminal heptad repeats of tropomyosin isoform 5. Arch. Biochem. Biophys. 378: 16-24.
Balamurugan et al. Surface Immobilization Methods for aptamer diagnostic applications Analytical and Bioanalytical Chemistry vol. 390 numb 4 Feb. 2008.
Wang et al. Aptamer biosensor for protein detection using gold nanoparticls Analytical Biochemistry vol. 373 issue 2 Feb. 2008.
Savran et al. Micromechanical Detection of Proteins Using Aptamer-Based Receptor Molecules. Anal. Chem. 76, 3194-3198, (2004).
Liss et al., An Aptamer-Based Quartz Crystal Protein Biosensor. Anal. Chem., 74, 4488-4495, (2002).

(Continued)

*Primary Examiner* — Galina M. Yakovleva
(74) *Attorney, Agent, or Firm* — Michael B. Einschlag

(57) ABSTRACT

Method for immobilizing a target microorganism or target chemical found in a mammal includes introducing into a gastrointestinal tract of the mammal immobilization particles including immobilization molecules capable of attaching to the target microorganism or the target chemical, which immobilization molecules are attached to one or more portions of a structure that is capable of inhibiting contact between tissues of the gastrointestinal tract and the target microorganisms or target chemicals attached to the immobilization molecules.

18 Claims, 6 Drawing Sheets

(56) References Cited

OTHER PUBLICATIONS

Sriamornsak et. al. Composite Film-Coated Tablets Intended for Colon-Specific Delivery of 5-Aminosalicylic Acid: Using Deesterified Pectin. Pharm Dev and Tech. 2003, vol. 8, No. 3, 311-318.
Hua Z. et al. Technology to Obtain Sustained Release Characteristics of Drugs after Delivered to the Colon. Journal of Drug Targeting. vol. 6, Issue 6, Jul. 1999, 439-448.
Rudolph M. et al. A new 5-ASA multi-unit dosage form for the therapy of ulcerative colitis. European Journal of Pharmaceutics and Biopharmaceutics. vol. 51, Issue 3, May 2001, 183-190.
Gupta, et al. A novel pH and time based multi unit potential colonic drug delivery system. I. Development. International Journal of Pharmaceutics. vol. 213, Issues 1-2, Feb. 1, 2001, 83-91.
Kim et. al. Selective immobilization of proteins on gold dot arrays and characterization using chemical force microscopy. J. of Colloid and Interface Science, vol. 334, 2009, pp. 161-166.
Tuerk, et al. Systematic evolution of ligands by exponential enrichment: RNA ligands to bacteriophage T4 DNA polymerase. Science. Aug. 3, 1990 249: 505-510.
Suo Z., et al. Efficient Immobilization and Patterning of Live Bacterial Cells. Langmuir 2008, 24, 4161-4167.
Schmid et al. Site-directed antibody immobilization on gold substrate for surface plasmon resonance sensors. Sensor and Actuators B: Chemical. vol. 113. Issue 1, 17 Jan. 2006, 297-303.
uan Eqp, et al. Affinity of monoclonal antibodies interpretation of the positive cooperative nature of anti-hCG hCG Interactions. Journal of Immunological Methods 140 (1991) 235-241.
uan Eqp, et al. Characterization of monoclonal antibodies physically adsorbed onto polystyrene latex particles. Journal pf Immunological Methods. 152 (1992) 191-199.
Sato et al., Integration of an Immunosorbant Assay System Analysis of Secretory Human Immunoglobulin A on Polystyrene Beads in a Microchip. Anal Chem. 2000, 72, 1144-1147.
Turkmen, et al. Phenylalanine Containing Hydrophobic Nanospheres for Antibody Purification. Biotechnol. Prog. 2008, 24, 1297-1303.
Qian, et al. Immobilization of Antibodies on Ultraflat Polystyrene Surfaces. Clinical Chemistry 46:9, 1456-1463. (2000).
Boyd et al., Application of Antibody Adsorbed Polyester Cloth for Rapid Screening of Elution Conditions for Antigen Immunopurification. Immunological Investigations, vol. 25, Issue 5&6 Sep. 1996, pp. 447-453.
Mosher, et al. Microminiaturized Immunoassays Using Atomic Force Microscopy and Compositionally Patterned Antigen Arrays. Anal. Chem. 1998, 70, 1233-1241.
Siiman et al. Covalently Bound Antibody on Polystyrene Latex Beads: Formation, Stability, and Use in Analysis of White Blood Cell Populations. Journal of Colloid and Interface Science 234, 44-58 (2001).
Karyakin et al. Oriented Immobilization of Antibodies onto the Gold Surfaces via Their Native Thiol Groups. Anal. Chem., 2000, 72(16), pp. 3805-3811.
Shamah et al. Complex Target SELEX. Accounts of Chemical Research. 130-138 Jan. 2008. vol. 41. No. 1.
Homann et al. Combinatorial selection of high affinity RNA ligands to live African trypanosomes. Nucleic Acids Research, 1999, vol. 27, No. 9.
Wang et al. In vitro selection of novel RNA ligands that bind human cytomegalovirus and block viral infection, RNA (2000) 6: 571-583.
Keefe et al. SELEX with modified nucleotides. Current Opinion in Chemical Biology 2008. 12: 448-456.
Hamula et al. Selection of Aptamers against Live Bacterial Cells. Anal. Chem. 2008, 80, 7812-7819.
Hall et al. In Vitro Selection of RNA Aptamers to a Protein Target by Filter Immobilization. Current Protocols in Molecular Biology 243.1-24.3.27. Oct. 2009.
Westall, et al. 1971. Essential chemical requirements for induction of allergic encephalomyelitis. Nature 229: 22-24.
Van Erp "Monoclonal antibodies in diagnostics. Monitoring of monoclonal antibody characteristics during (large scale) production, purification and application in diagnostic systems." Ph.D. Thesis, University of Nijmegen, Nijmegen, Netherlands, 1991 chap. 6.
A printout by an Examiner retrieved from http://en.wikipedia.org/wiki/Bacteria on Nov. 19, 2013.
Curtis, Chapter 4—Hygiene & Water Purification from "The Backpackers Field Manual by Rick Curtis," Random House Publishing & Rick Curtis, Outdoor Action Program, Princeton University, 1999, 4 pages.
Foley et al., "Concentration Gradient Immunoassay. 2. Computational Modeling for Analysis and Optimization," Anal. Chem., 2007, vol. 79, No. 10, pp. 3549-3553, Publication Date (Web): Apr. 17, 2007.
Jayasena, "Aptamers: An Emerging Class of Molecules That Rival Antibodies in Diagnostics," Clin. Chem., 1999, vol. 45, No. 9, pp. 1628-1650.
Suo et al., "Efficient Immobilization and Patterning of Live Bacterial Cells," Langmuir, 2008, 24, pp. 4161-4167.
Soloviev, "Nanobiotechnology today: focus on nanoparticles," Journal of Nanobiotechnology, 2007, 5:11.
Mukherjee et al., "Potential therapeutic application of gold nanoparticles in B-chronic lymphocytic leukemia (BCLL): enhancing apoptosis," Journal of Nanobiotechnology 2007, 5:4.
Ho et al., "Using Biofunctionalized Nanoparticles to Promote Pathogenic Bacteria," Anal. Chem. 2004, 76 (24), pp. 7162-7168.
Wikipedia reference in previous application, a print-out retrieved from https://en.wikipedia.org/wiki/Enema on Mar. 5, 2018.

* cited by examiner

USE OF IMMOBILIZATION PARTICLES FOR REMOVAL OF MICROORGANISMS AND/OR CHEMICALS

This patent application is a continuation of a U.S. patent application entitled "Use of Immobilization Particles for Removal of Microorganisms and/or Chemicals" having application Ser. No. 15/002,300 which was filed on Jan. 20, 2016, which patent application was a continuation of a U.S. patent application entitled "Immobilization Particles for Removal of Microorganisms and/or Chemicals" having application Ser. No. 13/344,315 which was filed on Jan. 5, 2012, which U.S. patent application is a continuation-in-part of a U.S. patent application entitled "Immobilization Particles for Removal of Microorganisms and/or Chemicals" having application Ser. No. 12/660,459 which was filed on Feb. 26, 2010 and which claimed priority under 35 U.S.C. 119(e) from a U.S. provisional patent application having Appl. No. 61/208,629 which was filed on Feb. 26, 2009 and a U.S. provisional patent application having Appl. No. 61/212,375 which was filed on Apr. 11, 2009, all of which prior patent applications are incorporated herein by reference in their entireties.

TECHNICAL FIELD

One or more embodiments relate to methods for removing microorganisms or chemicals.

BACKGROUND

The mixture of microorganisms in a person's gastrointestinal tract greatly affects the person's health. Some beneficial effects provided by the mixture of microorganisms are: aiding in food digestion, creating vitamins, sequestering and neutralizing toxic metals, creating anti-cancer compounds, secreting beneficial enzymes, and preventing pathogenic microorganisms from colonizing the gastrointestinal tract.

From the time a person is approximately one year old until s/he is in her/his 50's to 60's, the composition of the mixture of microorganisms, for example, bacteria, and the population thereof is mostly stable. A combination of genetics, bacterial exposure from the environment and a person's diet help determine the strains and quantities of bacteria that colonize the person's gastrointestinal tract. For most normal, healthy individuals, their microbial population, or microbiome, does not cause any problems. Unfortunately, for others, their microbiome becomes dysfunctional and creates various chronic health problems.

There are many triggers that cause a microbiome to become dysfunctional. One common trigger is the use of antibiotics and antifungals. Antibiotics and antifungals kill many kinds of bacteria and fungi, both helpful and harmful. When antibiotics and/or antifungals are taken into the body, beneficial bystander bacteria and/or fungi (i.e. bacteria or fungi that are not the intended target of the antibiotics or antifungals) get killed. As a result, the natural balance of microorganisms in the microbiome may be perturbed, and remaining beneficial bacteria and/or fungi can lose their ability to inhibit harmful ones. In addition, certain antibiotics can change the behavior of normally present bacteria and make them harmful or more difficult for the immune system or antibiotics to target. For example, Penicillin G makes Proteus bacteria become cell wall deficient, and as a result, many antibiotics cannot kill them.

Once a bacterial and/or fungal population is perturbed by antibiotics and/or antifungals, enzymes present in the gastrointestinal tract can change and the normal distribution of peptides seen by the immune system can change. If peptide sequences that sufficiently resemble various molecules of a host's organ or other tissue survive in sufficient concentrations, autoimmune disease may result.

SUMMARY

One or more embodiments solve one or more of the above-identified problems. In particular, one embodiment is a method for immobilizing a target microorganism or target chemical found in a mammal that comprises introducing into a gastrointestinal tract of the mammal immobilization particles comprising immobilization molecules capable of attaching to the target microorganism or the target chemical, which immobilization molecules are attached to one or more portions of a structure that is capable of inhibiting contact between tissues of the gastrointestinal tract and the target microorganisms or target chemicals attached to the immobilization molecules.

DETAILED DESCRIPTION

Figure 1:
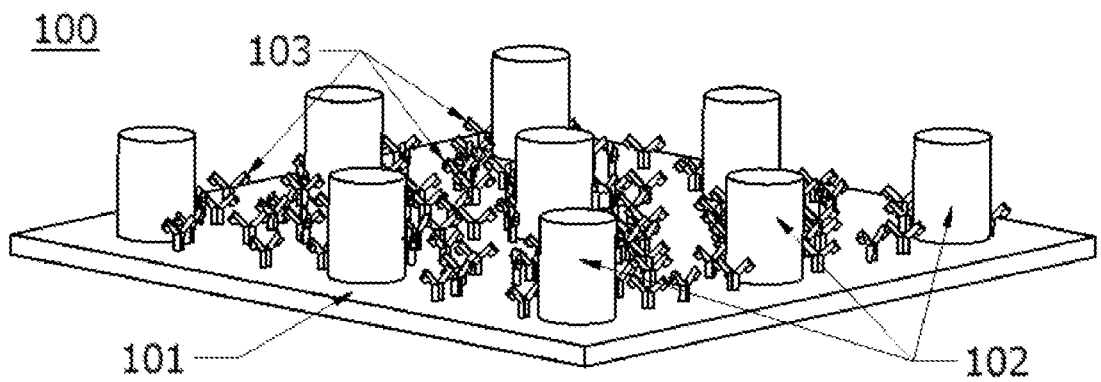
FIG. 1 shows a perspective view of an immobilization particle that is fabricated in accordance with one or more embodiments of the present invention.

One or more embodiments of this invention are immobilization particles that immobilize microbes and/or chemicals found, for example and without limitation, in a human's or in an animal's gastrointestinal tract. In accordance with one or more further embodiments of the present invention, such immobilization particles that are introduced into the gastrointestinal tract may be removed by natural processes and/or as aided by mechanical processes such as, but not limited to, enema, suction, or magnetic attraction.

In accordance with one or more embodiments of the present invention, a target microorganism and/or chemical becomes attached to an immobilization particle, and as a result, the target microorganism or chemical can be removed from the body. In accordance with one or more further embodiments, immobilization particle is constructed so the attached target microorganism and/or chemical does not physically interact with gastrointestinal tract tissue. In accordance with one or more such embodiments, for use of an immobilization particle to attach to a microorganism (as used herein, the terms microorganism and microbe are the same), the immobilization particle can remove the microbe without killing it and without the microbe breaking up into pieces. Advantageously, keeping a microbe whole and out of physical contact with a host's gastrointestinal tract tissue may help prevent an undesirable interaction with the host's immune system, which interaction may lead to harmful inflammation. In addition and in accordance with one or more further such embodiments of the present invention, for the case of a piece of a microorganism that could be immunologically active, the immobilization particle can remove the piece of microorganism before it causes unwanted reactions in the body. In addition and in accordance with one or more further such embodiments of the present invention, for the case of the use of an immobilization particle to attach to a chemical, the immobilization particle can remove the chemical before it causes unwanted reactions. Such unwanted reactions may, for example and without limitation, produce concentrations enzymes that, in turn, can cause abnormal concentrations of peptide sequences which, in turn, may cause an autoimmune reaction. As such, an immobilization particle that is fabricated in accordance with one or more embodiments of the present invention may be used to remove triggers autoimmune disease and its symptoms, which triggers, for example and without limitation, may be peptide sequences that resemble portions of human tissue.

In accordance with one or more embodiments of the present invention, an immobilization particle comprises a substrate structure comprised of a substrate that includes one or more concave surfaces, one or more recesses, and/or one or more pores. In accordance with one or more such embodiments, an immobilization particle further comprises immobilizing molecules attached to at least a portion of the surface of the substrate. In accordance with one or more further embodiments of the present invention, an immobilization particle comprises a substrate structure wherein spacer structures are affixed to the substrate and wherein the spacer structures are adapted to inhibit contact between the immobilization molecules and tissue such as, for example and without limitation, tissue or mucosa of the gastrointestinal wall. As such, in providing spacer structures, one would take into account the size of immobilization molecules and a size of a target microorganism or a chemical. In accordance with one or more such embodiments, the substrate structure further comprises a substrate support with is attached to the substrate, wherein the spacer structures are affixed to the substrate or to the substrate support.

Figure 2:
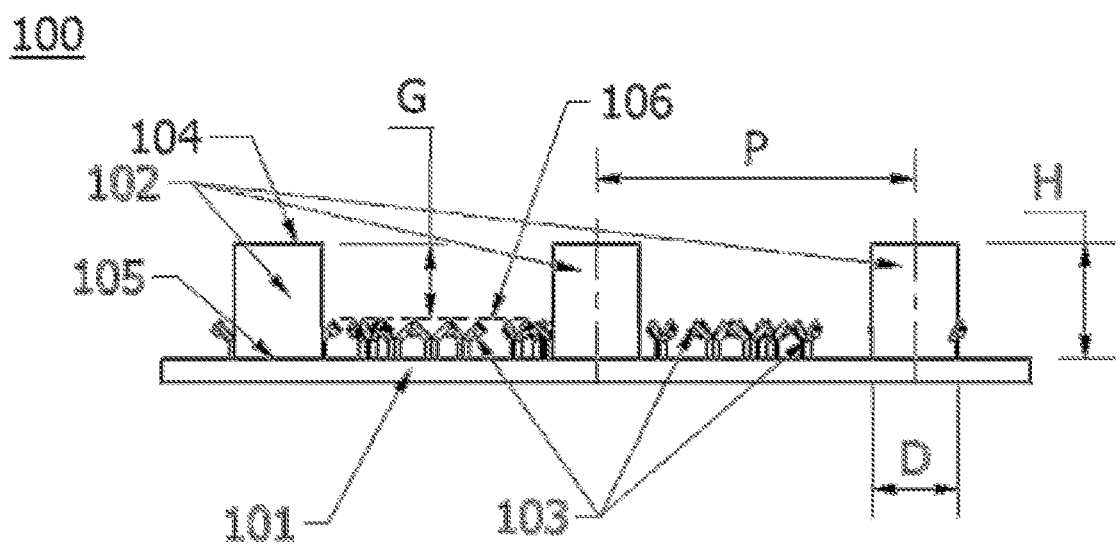
FIG. 2 shows a side view of the immobilization particle shown in FIG. 1.

FIG. 1 shows a perspective view of immobilization particle 100 that is fabricated in accordance with one or more embodiments, and FIG. 2 shows a side view of immobilization particle 100. As shown in FIG. 1, immobilization particle 100 includes (a) a substrate structure comprised of substrate 101 and spacers 102; and (b) immobilization molecules 103. As shown in FIG. 1, substrate 101 is planar and spacers 102 and immobilization molecules 103 are attached to substrate 101. Spacers 102 are sufficiently tall, and spaced closely enough together so that, in a particular application, they are capable of inhibiting physical contact between tissue, for example and without limitation, tissue from a flexible gastrointestinal wall and/or dendritic cells attached to the gastrointestinal wall and target microorganisms and/or chemicals attached to immobilization molecules 103. In operation, the top surfaces of spacers 102 push the host's tissues away from surfaces of substrate 101 where the immobilization molecules are attached. As shown in FIG. 2, spacers 102 have a height H and a width D, the distance between the centers of spacers 102 is P, and the distance between immobilization particles 103 and the top of spacers 102 is G. For example, H is large enough so that a target microorganism or chemical can attach to immobilization molecules 103 without the target microorganism or target chemical coming into physical contact with the host's tissues. Appropriate height and/or spacing for spacers 102 for a particular application can be determined routinely by one of ordinary skill in the art without using undue experimentation. For example, appropriate height and spacing depends, among other things on the particular immobilization molecule, and the targeted microorganism and/or chemical, and the particular tissue whose touch is to be inhibited or avoided. In some applications, the taller spacers 102 are, the farther apart they can be. It should be understood by those of ordinary skill in the art that further embodiments exist where the heights of spacers 102 may be different, and/or the distances between spacers 102 may be different, and/or immobilization molecules 103 may be different. In accordance with one or more embodiments, the height of spacers is in a range from about 0.01 microns to about 500 microns and the distance between spacers is in a range from about 0.1 microns to about 500 microns.

In accordance with one or more embodiments, substrate 101 and spacers 102 can be made of, for example and without limitation, one or more of the following materials: polymer, metal, ceramic, semiconductor, carbohydrate, polysaccharide, polypeptide, protein, glycolipid, gel, highly viscous glass or a combination or composite of one or more of the foregoing. Examples of suitable polymers include, for example and without limitation, one or more of silicone, polyethylene, polystyrene, polyurethane, polymethacrylate, polyester, and polycarbonate. In accordance with one or more further embodiments of the present invention, the substrate and spacers are comprised of a polymer film such as, for example and without limitation, Mylar or a woven or compressed polyester fabric. The materials can be molded, chemical vapor deposited, physical vapor deposited, ground, etched, extruded, solution precipitated, blown, vapor phase reacted, crushed, tumbled, polished, chemical mechanical planarized, electro discharge machined, pressed, stamped, lased, machined, poured, spun, pulled, pressed, welded, bonded, diffusion bonded, friction bonded, ultrasonically welded, ion beam welded, ion beam deposited, punched, pressure formed, gouged, cut, laser cut, abrasive blasted, freeze fractured, chemically foamed and cooled, cured, UV cured, photo-lithographed, 3D printed, stereo-lithographed, silk-screened, ink jet printed, fused, or made using any combination of the previously mentioned processes, which processes are well known to those of ordinary skill in the art.

Figure 3:
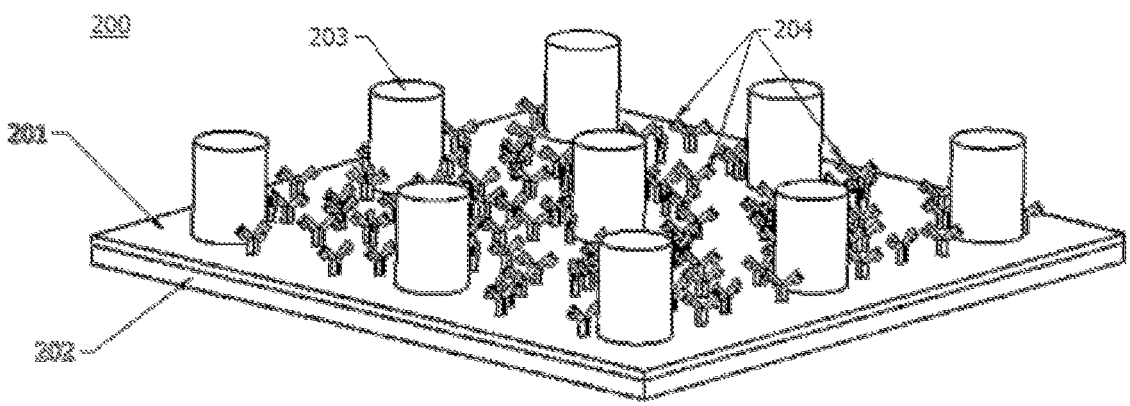
FIG. 3 shows a perspective view of an immobilization particle that is fabricated in accordance with one or more further embodiments.
Figure 4:
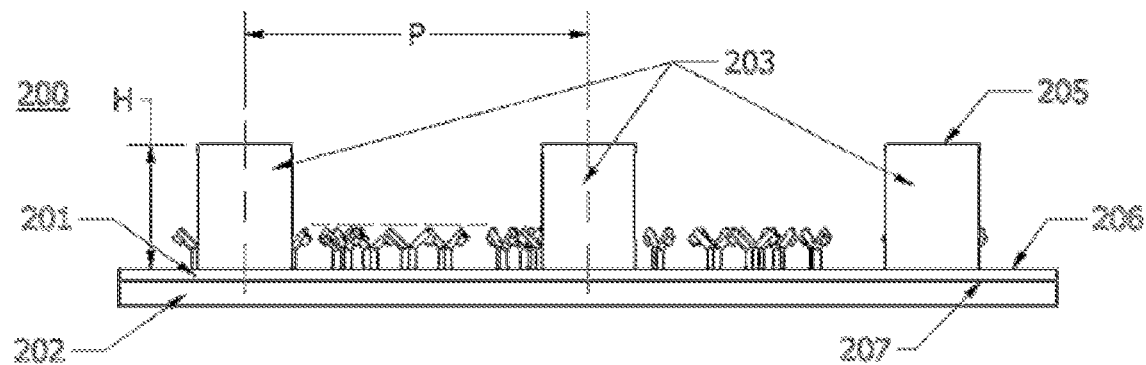
FIG. 4 shows a side view of the immobilization particle shown in FIG. 3.

FIG. 3 shows a perspective view of immobilization particle 200 that is fabricated in accordance with one or more further embodiments, and FIG. 4 shows a side view of immobilization particle 200. As shown in FIG. 3, immobilization particle 200 includes (a) a substrate structure comprised of substrate 201, planar substrate support 202 and spacers 203; and (b) immobilization molecules 203. As shown in FIG. 3, substrate 201 is planar. As indicated in FIG. 3, spacers 203 are attached to substrate support 202, and immobilization molecules 204 are attached to substrate 201. It should be understood by those of ordinary skill in the art that further embodiments exist where spacers 203 are attached to substrate 201. Spacers 203 are sufficiently tall, and spaced closely enough together, so that, in a particular application, they are capable of inhibiting physical contact between tissue, for example and without limitation, tissue from a flexible gastrointestinal wall and/or dendritic cells attached to the gastrointestinal wall and microorganisms and/or chemicals attached to immobilization molecules 204. In operation, the top surfaces of spacers 203 push the host's tissues away from surfaces of substrate 201 where immobilization molecules 204 are attached. As shown in FIG. 4, spacers 203 have a height H and a width D, the distance between the centers of spacers 203 is P, and the distance between immobilization particles 204 and the top of spacers 203 is G. For example, H is large enough so that a target microorganism or chemical can attach to immobilization molecules 204 without the target microorganism or target chemical coming into contact with the host's tissues. Appropriate height and/or spacing for spacers 203 for a particular application can be determined routinely by one of ordinary skill in the art without using undue experimentation. For example, appropriate height and spacing depends, among other things on the particular immobilization molecule, and the targeted microorganism and/or chemical, and the particular tissue whose touch is to be inhibited or avoided. It should be understood by those of ordinary skill in the art that further embodiments exist where the heights of spacers 203 are different, and/or the distances between spacers 203 are different, and/or immobilization molecules 204 are different. In accordance with one or more embodiments, the height of spacers is in a range from about 0.01 microns to about 500 microns and the distance between spacers is in a range from about 0.1 microns to about 500 microns.

In accordance with one or more such embodiments, substrate 201 is attached to substrate support 202, and substrate support 202 is thick enough to enable substrate 201 to maintain a predetermined shape. In accordance with one or more such embodiments, substrate 201 and substrate support 202 may be fabricated from the same materials set forth above for substrate 101, spacers 203 may be fabricated from the same materials set forth above for spacers 102, and substrate 201, substrate support 202 and spacers 203 may be fabricated using the same methods set forth above for substrate 101 and spacers 102. In accordance with one or more such embodiments, substrate 201 and substrate support 202 can be the same material or a different material, also, substrate 201 may be a coating which is deposited on substrate support 202.

Figure 5:
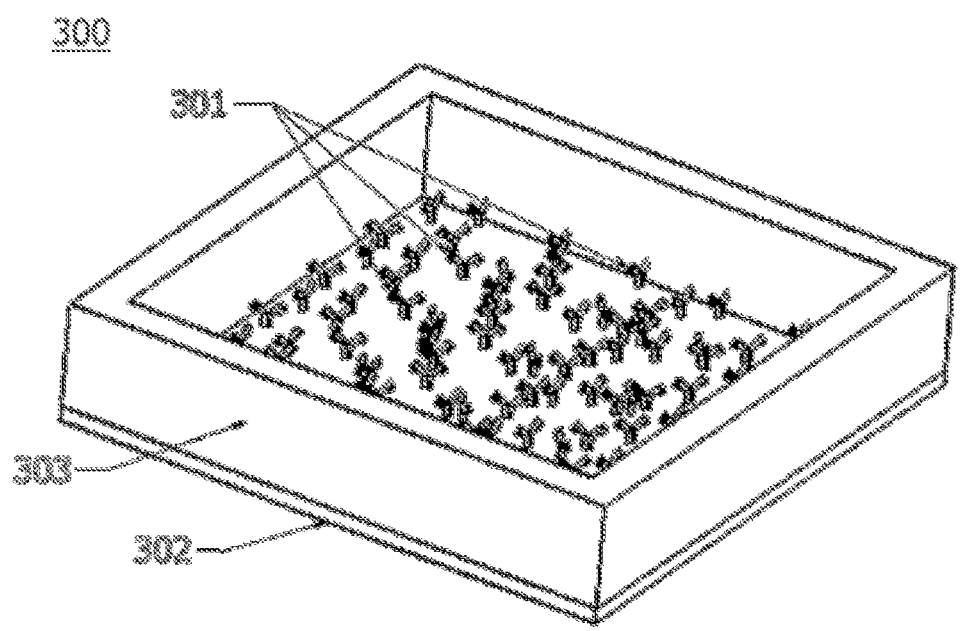
FIG. 5 shows a perspective view of an immobilization particle that is fabricated in accordance with one or more still further embodiments.
Figure 6:
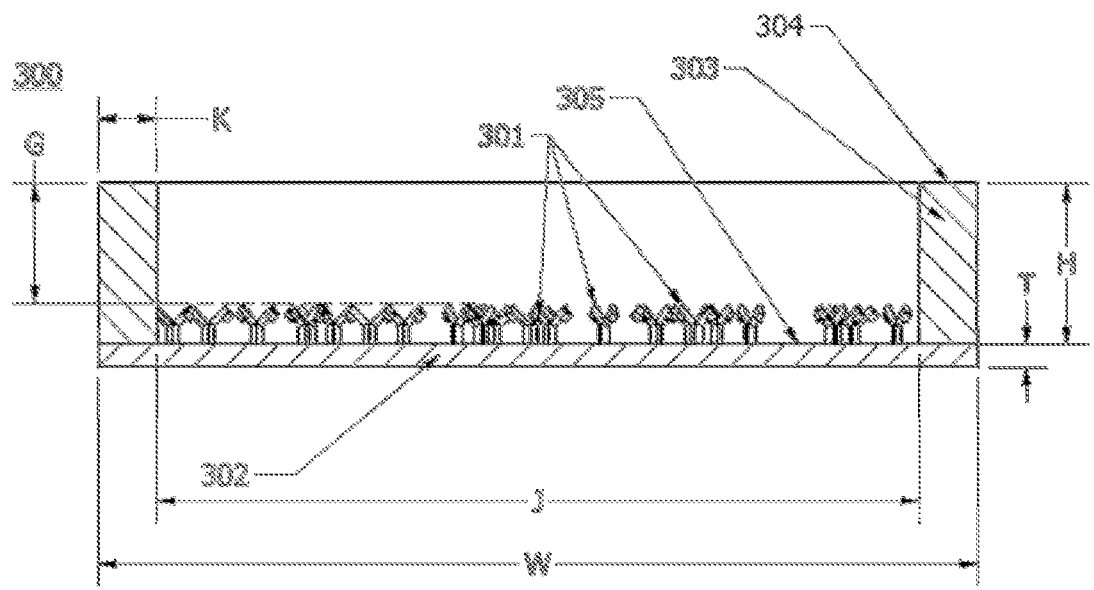
FIG. 6 is a side view of the immobilization particle shown in FIG. 5.

FIG. 5 shows a perspective view of immobilization particle 300 that is fabricated in accordance with one or more still further embodiments, and FIG. 6 is a side view of the immobilization particle shown in FIG. 5. As shown in FIG. 5, immobilization particle 300 includes (a) a substrate structure comprised of substrate 302 and spacer 303; and (b) immobilization molecules 301. As shown in FIG. 5, substrate 302 is planar and spacer 303 and immobilization molecules 301 are attached to substrate 302. As shown in FIG. 5, spacer 303 is formed as a wall that surrounds a predetermined area of substrate 302. The walls of spacer 303 are sufficiently tall, and are spaced closely enough together so that, in a particular application, they are capable of inhibiting physical contact between tissue, for example and without limitation, tissue from a flexible gastrointestinal wall and/or dendritic cells attached to the gastrointestinal wall and target microorganisms and/or chemicals attached to immobilization molecules 301. In operation, top surfaces 304 of spacer 303 push the host's tissues away from surface 305 of substrate 302 where immobilization molecules 301 are attached. Although the walls of spacer 303 form a square, it should be understood by those of ordinary skill in the art that further embodiments exist where the walls of spacer 303 form a rectangle and other embodiments exist where the walls of spacer 303 form a polygon such as a triangle, or even form a curvilinear shape such as, for example and without limitation, a cylinder. As shown in FIG. 6, the walls of spacer 303 have a height H, a width K, the distance between the outer edges of the walls is W, and the distance between the inner edges of the walls is J, and the distance between immobilization particles 301 and the top surface of the walls is G. For example, H is large enough and J is small enough so that a target microorganism or target chemical can attach to immobilization molecules 301 without the target microorganism or target chemical coming into contact with the host's tissues. Appropriate height and/or spacing for the walls of spacer 303 for a particular application can be determined routinely by one of ordinary skill in the art without using undue experimentation. For example, appropriate height and spacing depends, among other things on the particular immobilization molecule, and the targeted microorganism and/or chemical, and the particular tissue whose touch is to be inhibited or avoided. In accordance with one or more embodiments, the height of walls is in a range from about 0.01 microns to about 500 microns and the distance between walls is in a range from about 0.1 microns to about 500 microns. It should be understood by those of ordinary skill in the art that further embodiments exist where an immobilization particle comprises several units like that shown in FIGS. 5 and 6, and that in such further embodiments the heights of the walls of the various spacers may be different, and/or the shapes of the walls of the spacers may be different, and/or immobilization molecules 301 in the various units may be different. In addition, further embodiments exist where the walls of spacer 303 are not continuous, but are comprised of discontinuous segments. Still further embodiments exist where the walls of spacer 303 and the perimeter of substrate 302 are not aligned and where the perimeter of substrate 302 is not rectangular. Yet still further embodiments exist where the height H of top surface 304 of the walls of spacer 303 vary—for example and without limitation, top surface 304 may a wavy surface.

As one of ordinary skill in the art can readily appreciate, by attaching spacer 303 to substrate 302, a concave-shaped immobilization particle is formed such that surface 305 of substrate 302 may be viewed as an inner concave surface of immobilization particle 300. The interior surfaces of concave cavities are preferred surfaces to which immobilization molecules are attached. This is because targets, such as, for example and without limitation, single celled organisms or parts of organisms, captured by immobilization molecules attached to interior surfaces of a concave cavity are shielded from physical contact with surfaces of a host's gastrointestinal wall by the concave cavity. In addition, the concave cavity makes it more difficult for tentacles of dendritic cells in the host's gastro-intestinal wall to reach targets captured within the concave cavity. It is believed that preventing physical contact with the target is beneficial in that it prevents a host's immune system from becoming aware of the target's presence. This, in turn, prevents the host's immune system from generating an immune response by generating cross-reacting antibodies to the immobilized targets, which antibodies could, in the case of autoimmunity, attack other body tissues.

In accordance with one or more such embodiments, substrate 302 and spacer 303 may be fabricated from the same materials set forth above for substrate 101, and substrate 302 and spacers 303 may be fabricated using the same methods set forth above for substrate 101 and spacers 102. It should also be understood that further embodiments exist where the substrate structure includes a substrate support that is fabricated in the same manner described above with respect to immobilization particle 200.

Figure 7:
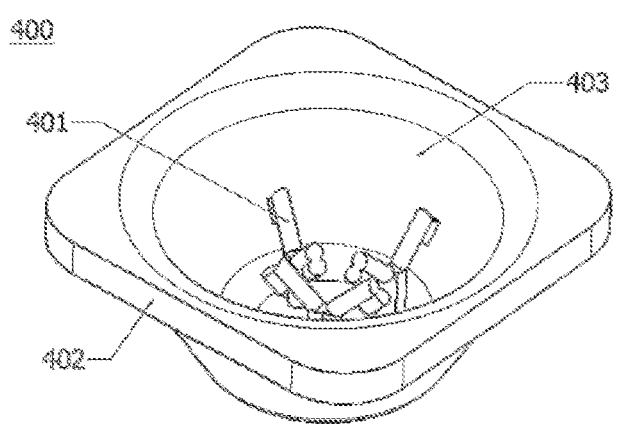
FIG. 7 shows a perspective view of an immobilization particle that is fabricated in accordance with one or more still further embodiments.

FIG. 7 shows a perspective view of immobilization particle 400 that is fabricated in accordance with one or more further embodiments. As shown in FIG. 7, immobilization particle 400 includes (a) a substrate structure comprised of substrate 402 which includes a concavity, with concave surface 403, within substrate 402; and (b) immobilization molecules 401 attached to concave surface 403. As shown in FIG. 7, a surface of substrate 402 surrounding the opening of the concavity is substantially planar, and the shape of the opening of the concavity is substantially circular. In accordance with one or more such embodiments, the depth at which immobilization molecules 401 are attached to concave surface 403 (as measured from the surface of substrate 402 that surrounds the opening of the concavity) is sufficiently large so that, in a particular application, tissue, for example and without limitation, tissue from a flexible gastrointestinal wall and/or dendritic cells attached to the gastrointestinal wall is capable of being inhibited from making physical contact with target microorganisms and/or chemicals attached to immobilization molecules 401. In operation, immobilization top surfaces of substrate 402 surrounding the cavity push the host's tissues away from concave surface 403 where immobilization molecules 401 are attached. In accordance with one or more embodiments, concave surface 403 has a depth in a range from about 0.02 microns to about 3000 microns, and immobilization molecules are affixed at depths in a range from about 0.01 microns to about 3000 microns.

In accordance with one or more such embodiments, substrate 402 may be fabricated from the same materials set forth above for substrate 101. It should also be understood that further embodiments exist where the substrate structure includes a substrate support disposed on substrate 402 in the manner described above with respect to immobilization particle 200. It should also be understood that further embodiments exist where the opening of the concavity in substrate 402 has a non-circular shape such as, for example and without limitation, an elliptical shape, the shape of a kidney bean, or other shapes. It should also be understood that further embodiments exist wherein the surface of the opening of the concavity in substrate 402 is non-planar.

Figure 8:
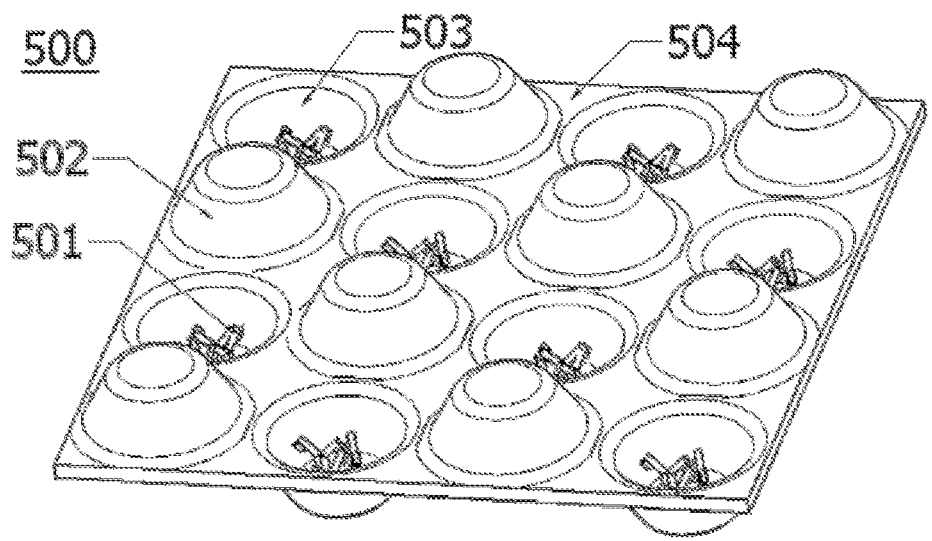
FIG. 8 shows a perspective view of an immobilization particle fabricated as an array of the immobilization particle shown in FIG. 7.

FIG. 8 shows a perspective view of immobilization particle 500 that is fabricated in accordance with one or more further embodiments. As shown in FIG. 8, immobilization particle 500 includes a substrate structure comprised of substrate 504 which includes an array of concavities disposed so that openings of the concavities are alternately disposed at a top surface and a bottom surface of substrate 504, respectively. In addition, as shown in FIG. 8, the concavities are formed so that they provide a convexities in substrate 504 on a surface of 504 opposite from their openings. In accordance with one or more such embodiments, one or more such concavities is like the concavity described above with respect to immobilization particle 500.

As such, as shown in FIG. 8, immobilization molecules 501 are attached to concave surface 503. Although not shown in FIG. 8, in accordance with one or more embodiments, immobilization molecules may be attached to concave surfaces 503 at any depth with respect to the opening thereof, as well as, at planar portions of substrate 504. In accordance with one or more such embodiments, convex surfaces, like convex surface 502 of an adjacent concavity in substrate 504 functions as a spacer. In accordance with one or more such embodiments, the height of convex surfaces 502 above planar portions of substrate 504 are sufficiently tall, and are spaced closely enough together, so that, in a particular application, convex surfaces 502 are capable of inhibiting physical contact between tissue, for example and without limitation, tissue from flexible gastrointestinal wall and/or dendritic cells attached to the gastrointestinal wall and microorganisms and/or chemicals attached to immobilization molecules 501. In operation, convex surface 502 pushes the host's tissues away from surfaces 503 and 504 where immobilization molecules 501 are attached. Although convex surfaces 502 and concave surfaces 503 are shown in FIG. 8 as tapered conical surfaces, it should be understood by those of ordinary skill in the art that further embodiments exist where surfaces 503 and 502 are polygonal or even have a rectilinear shape such as, for example and without limitation, a box or pyramidal shape. A depth of concave surface 503 should be sufficiently deep so that target microorganisms and/or chemicals can attach to immobilization molecules 501 without coming into contact with the host's tissues. Appropriate height and/or spacing for concave surfaces 503 and convex surfaces 502 for a particular application can be determined routinely by one of ordinary skill in the art without using undue experimentation. For example, appropriate height and spacing depends, among other things on the particular immobilization molecule, the targeted microorganism and/or chemical, and the particular tissue whose touch is to be inhibited or avoided. In accordance with one or more embodiments, the depths of the concavities and convexities are in a range from about 0.02 microns to about 3000 microns, and a distance between adjacent concavities and convexities is in a range from about 0.1 microns to about 5000 microns. It should be understood by those of ordinary skill in the art that further embodiments exist where an immobilization particle is attached to concave surfaces and the depths of the concave surfaces and heights of the convex surfaces are different, and/or the shapes of concave surfaces 503 and convex surfaces 502 are different. In addition, further embodiments exist where the spacing between repeated concave and convex surfaces is irregular and/or do not line up in a rectilinear fashion.

Figure 9:
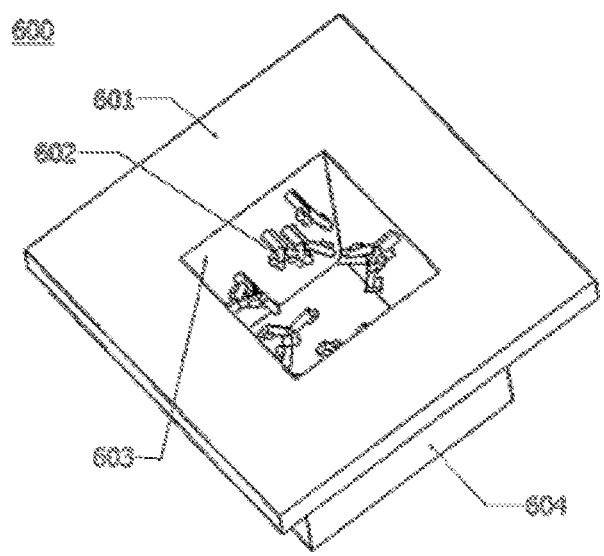
FIG. 9 shows a perspective view of an immobilization particle that is fabricated in accordance with one or more still further embodiments.

FIG. 9 shows a perspective view of immobilization particle 600 that is fabricated in accordance with one or more further embodiments. As shown in FIG. 9, immobilization particle 600 is the same as immobilization particle 400 described above in conjunction with FIG. 7 except that the concavity of immobilization particle 600 has a shape like that of immobilization particle 300 described above in conjunction with FIG. 5. As shown in FIG. 9, immobilization molecules are not attached to flange 601 which surrounds wall 603. It should be understood that further embodiments exist where the substrate structure of immobilization particle 600 includes a substrate support in the same manner described above with respect to the substrate support of immobilization particle 200.

Figure 10:
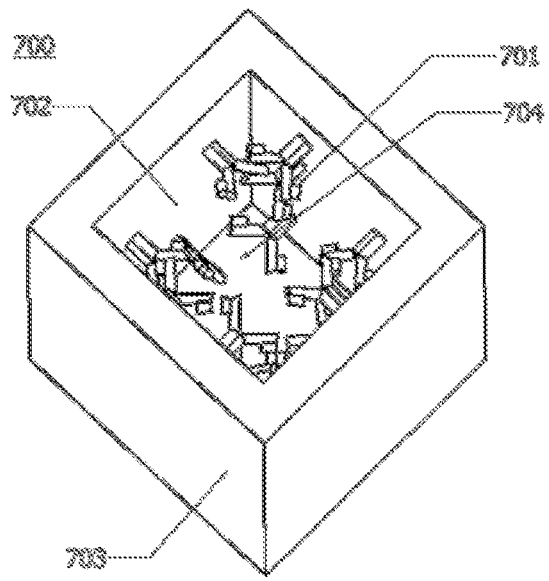
FIG. 10 shows a perspective view of an immobilization particle that is fabricated in accordance with one or more still further embodiments.

FIG. 10 shows a perspective view of immobilization particle 700 that is fabricated in accordance with one or more further embodiments. As shown in FIG. 10, immobilization particle 700 includes (a) a substrate structure comprised of wall 703 that surrounds hollow space 704; and (b) immobilization molecules 701 attached to inner concave surfaces 702 of wall 703. As further shown in FIG. 10, the substrate structure of immobilization particle 700 has open ends that enable target microorganisms and/or chemicals to enter hollow space 704 where they become attached to immobilization molecules 701. In accordance with one or more such embodiments, immobilization molecules 701 are attached sufficiently far from the open ends of the hollow space 704 so that attached target microorganisms and/or chemicals do not interact with a host's tissues as discussed above. Although FIG. 10 shows wall 703 having four interior sides which form a closed structure surrounding hollow space 704, it should be understood that further embodiments exist where wall 703 has three or more sides that form a polygonal wall structure about hollow space 704. In addition, in still further embodiments, the sides of the wall may be curvilinear instead of being planar. In addition, yet still further embodiments exist where a substrate support may be attached to outer surfaces of the sides of wall 703. In accordance with one or more such embodiments, immobilization particle 700 may be fabricated from the same materials set forth above for immobilization particle 300.

Figure 11:
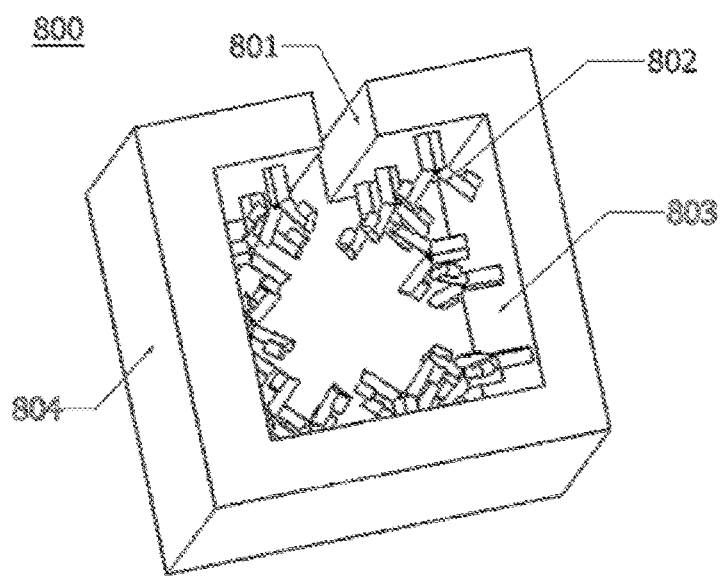
FIG. 11 shows a perspective view of an immobilization particle that is fabricated in accordance with one or more still further embodiments.

FIG. 11 shows a perspective view of immobilization particle 800 that is fabricated in accordance with one or more further embodiments. As shown in FIG. 11, immobilization particle 800 is the same as immobilization particle described above in conjunction with FIG. 10 except that wall 804 includes slot 801. Slot 801 enables target microorganisms and/or chemicals to enter the hollow space and attach to immobilization molecules 802. The width of slot 801 is sufficient to permit the entrance of target microorganisms and/or chemicals. It should be understood that embodiments exist where slot 801 does not extend along the entire length of wall 804. Appropriate width and length for slot 801 for a particular application can be determined routinely by one of ordinary skill in the art without using undue experimentation. In accordance with one or more embodiments, slot 801 has a width in a range from about 0.5 microns to about 100 microns, and a length in a range from about 1 micron to about 5000 microns.

Figure 12:
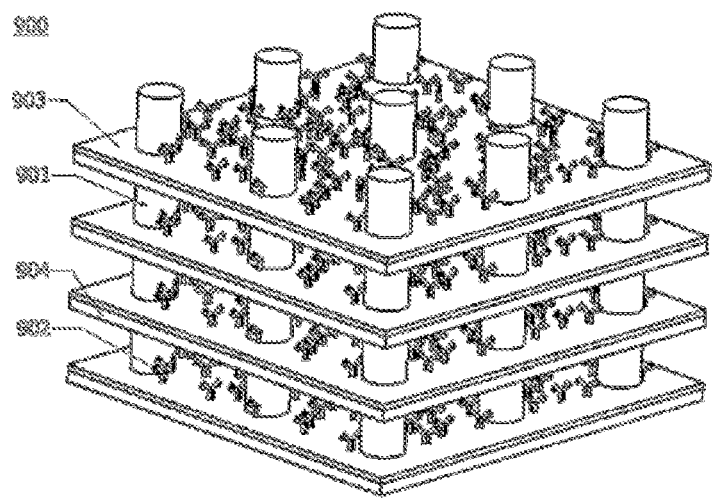
FIG. 12 shows a perspective view of an immobilization particle that is fabricated in accordance with one or more still further embodiments.

FIG. 12 shows a perspective view of immobilization particle 900 that is fabricated in accordance with one or more further embodiments. As shown in FIG. 12, immobilization particle 900 includes (a) a substrate structure comprised of multiple, spaced units, which units include substrate 903, substrate support 904 and spacers 901; and (b) immobilization molecules 902. Spacers 901 are sufficiently tall to permit the entrance of target microorganisms and/or chemicals into the units where they become attached to immobilization molecules 902. Substrate supports 904 are sufficiently thick to enable substrates 903 to maintain a predetermined shape. Appropriate height for spacers 901 and thickness for substrate supports 904 for a particular application can be determined routinely by one of ordinary skill in the art without using undue experimentation. In accordance with one or more such embodiments, the height of spacers 901 is in a range from about 0.01 micron to about 500 microns and the thickness of substrate supports 904 is in a range from about 1 micron to about 500 microns. In accordance with one or more such embodiments, spacers 901, substrates 903, and substrate supports 904 may be fabricated from the same materials set forth above for spacers 203, substrate 201, and substrate support 202. It should also be understood by those of ordinary skill in the art that further embodiments exist where substrates 903 are attached to both sides of substrate supports 904, and that this enables immobilization molecules 902 to be attached to substrates on either side of a gap created by spacers 901.

Figure 13:
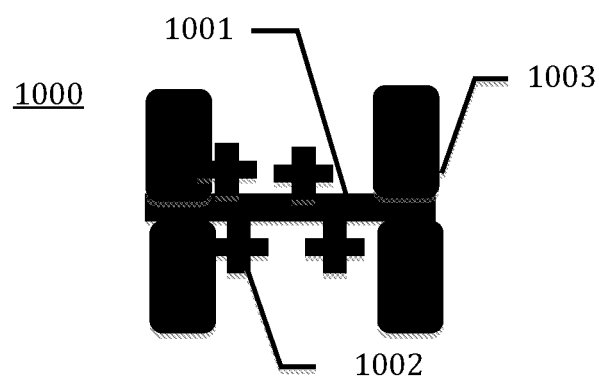
FIG. 13 shows a cross-section of an immobilization particle that is fabricated in accordance with one or more still further embodiments.

FIG. 13 shows a cross-section view of immobilization particle 1000 that is fabricated in accordance with one or more further embodiments of the present invention. As shown in FIG. 13, immobilization particle 1000 includes (a) a substrate structure comprised of substrate 1001 and spacers 1003; and (b) immobilization molecules 1002. Substrate 1001 is substantially planar; immobilization molecules 1002 are attached to both sides of substrate 1001; and spacers 1003 are attached to both sides of substrate 1001. Having immobilization molecules 1002 and spacers 1003 attached to both sides of substrate 1001 simplifies manufacturing because substrate 1001 can be completely immersed while attaching immobilization molecules 1002. In accordance with one or more such embodiments, substrate 1001 and spacer 1003 may be fabricated from the same materials set forth above for spacers 102, and substrate 1001 and spacers 1003 may be fabricated using the same methods set forth above for substrate 102 and spacers 103. It should also be understood that further embodiments exist where the substrate structure of immobilization particle 1000 includes a substrate support in the same manner described above with respect to immobilization particle 200. Appropriate height and spacing of spacers 1003 depends, among other things, on the particular immobilization molecule, the targeted microorganism and/or chemical, and the particular tissue whose touch is to be inhibited or avoided. It should be understood by those of ordinary skill in the art that further embodiments exist where an immobilization particle comprises several units like that shown in FIGS. 5 and 6, and that in such further embodiments the heights of the walls of the various spacers may be different, and/or the shapes of the walls of the spacers may be different, and/or immobilization molecules 1002 in the various units may be different.

Immobilization Molecules

In accordance with one or more embodiments of the present invention, an immobilization molecule is, for example and without limitation, an antibody or an aptamer. Antibodies are molecules that are produced by an immune system that attach specifically to microorganisms and chemicals (microorganisms can also produce antibodies). Antibodies are fairly large proteins (for example, a typical protein weighs approximately 150 kDa), and suitable antibodies can be created which are capable of binding to specific proteins or specific chemicals. Antibodies used to fabricate one or more embodiments of the present invention may be produced using standard monoclonal or polyclonal antibody production techniques that are well known to those of ordinary skill in the art. Aptamers are synthetic molecules that can attach to microorganisms and chemicals with high specificity. Suitable aptamers can be chemically synthesized bits of single-stranded RNA or DNA molecules or peptides whose selection is optimized by sorting processes that are well known to those of ordinary skill in the art. An example of such a sorting process is, but not limited to, a sorting process referred to as "Systematic Evolution of Ligands by Exponential Enrichment (SELEX)" in an article by Tuerk, et al. entitled "Systematic evolution of ligands by exponential enrichment: RNA ligands to bacteriophage T4 DNA polymerase." in *Science,* 3 Aug. 1990, 249, pp. 505-510. Aptamers are typically 100 nucleotides long. In accordance with one or more embodiments, a particular antibody and/or aptamer is selected for use with an intended target microorganism or chemical.

In accordance with one or more such embodiments, immobilization molecules can be attached to a substrate structure by adsorption or by covalent linking. For adsorbing an immobilization molecule to a substrate structure, one option is to place the substrate structure into a liquid containing an aptamer or antibody for a time long enough for the aptamer or antibody to be adsorbed onto the substrate structure. For proper adsorption, the substrate structure needs to be clean enough so that adsorption occurs, which level of cleanliness may be determined readily by one of ordinary skill in the art without undue experimentation.

Antibody Selection/Design—For Immobilizing Bacteria, Fungi, and Viruses: In accordance with one or more embodiments of the present invention, immobilization molecule(s) are antibodies and/or their fragment antigen binding, which fragment antigen binding is a region of the antibody that binds to an antigen. In accordance with one or more such embodiments, the immobilization molecules are antibodies and/or their fragment antigen binding that are useful to immobilize, for example and without limitation, one or more of the following genera of bacteria (use of such immobilization particles provides a method of treating or mitigating symptoms of diseases associated with such genera of bacteria): (a) for Multiple Sclerosis, the following genera of bacteria, *Enterococcus, Streptococcus, Lactobacillus, Bacteroides, Escherichia, Clostridium, Serratia, Bifidobacterium* and *Fusobacterium*; (b) for ulcerative colitis, the following genera of bacteria, *Burkholderia, Mycobacterium, Bacillus, Clostridium* and *Methylobacterium*; (c) for Lupus, the following genera of bacteria, *Burkholderia, Mycobacterium, Pseudomonas, Methylobacterium, Vibrio* and *Clostridium*; (d) for Uveoretinitis, the following genera of bacteria, *Bacteriodes, Bacillus, Clostridium, Lactobacillus, Fusobacterium, Vibrio, Ruminococcus* and *Methylococcus*; and (e) for rheumatoid arthritis, the following genera of bacteria, gram positive bacteria. It is believed that removing these genera of bacteria from a host is useful as they can exacerbate symptoms corresponding to the identified diseases. Suitable antibodies which can serve as immobilization molecules to immobilize the above-identified genera of bacteria are readily commercially available, for example and without limitation, BacTrace Anti-*Vibrio* Genus Antibody is a suitable antibody that is available from Kirkegaard & Perry Laboratories, Inc. (accessible at http://www.kpl.com).

In accordance with one or more further embodiments of the present invention, antibodies and/or their fragment antigen binding are selected to immobilize, for example and without limitation, one or more of the following genera of fungi: *Saccharomyces* and *Candida*. Suitable antibodies which can serve as immobilization molecules to immobilize the above-identified genera of fungi are readily commercially available, for example and without limitation, *Candida albicans* (BGN/03/5424) Species Antibody is a suitable antibody that is available from Santa Cruz Biotechnology, Inc. (accessible at http://www.scbt.com).

In accordance with one or more further embodiments of the present invention, antibodies and/or their fragment antigen binding are selected/designed to immobilize, for example and without limitation, one or more of the following viruses: Influenza, Herpes and Cytomegalovirus. Suitable antibodies which can serve as immobilization molecules to immobilize the above-identified genera of viruses are readily commercially available, for example and without limitation, Influenza A m1 (156-02) Antibody is a suitable antibody that is available from Santa Cruz Biotechnology, Inc. (accessible at http://www.scbt.com).

Antibody Adsorption onto Polymer: In accordance with one or more embodiments of the present invention, antibodies are attached to a polymer substrate structure by adsorption using the following steps. First, purify the antibody. Next, carry out an optional acid pretreatment of the antibody. Next, clean the substrate structure as described below. Next, adsorb the antibody onto the polymer substrate structure as described below.

Purification of the Antibody: In accordance with one or more embodiments of the present invention, antibodies and/or their fragment antigen binding are purified using, for example and without limitation, the following method: sodium sulphate precipitation (20% w/v) followed by Sephacryl S-200 HR gel filtration or protein A affinity chromatography, which method is disclosed in an article by van Erp entitled "Monoclonal antibodies in diagnostics. Monitoring of monoclonal antibody characteristics during (large scale) production, purification and application in diagnostic systems." Ph.D. Thesis, University of Nijmegen, Nijmegen, Netherlands, 1991 available at the University of Nijmegen Library, Nijmegen, Netherlands, and an article by van Erp et al. entitled "Affinity of monoclonal antibodies: Interpretation of the positive cooperative nature of anti-hCG/hCG interactions. *J. Immunol. Methods,* 140, 1991, pp. 235-241.

Acid Pretreatment of Antibody: As disclosed in an article by van Erp et al. entitled "Characterization of monoclonal antibodies physically adsorbed onto polystyrene latex particles" in *J. of Immunol. Methods,* 152 pp. 191-199, 1992, pre-treating antibodies with hydrochloric acid, or an acid solution with a pH of approximately 1.0-3.0, can improve the binding capacity of antibodies to substrate structures. In accordance with one or more embodiments of the present invention a pretreatment comprises, for example and without limitation: (a) mixing antibodies with 0.05M glycine/HCl buffer pH 2.0; (b) incubating the antibody solution at 0-4 degrees Celsius for 1 hour; and (c) adjusting the pH of the mixture to 6.0-8.0 by the addition of 0.1 M NaOH.

Cleaning Polymer Substrate structures: In accordance with one or more embodiments of the present invention, substrate 101, substrate 201 and substrate 302 described above may be a polymer such as, for example and without limitation, polystyrene, polyester or nylon, and may require cleaning. Top surface 105 of substrate 101, top surface 206 of substrate 201 and top surface 305 of substrate 302 can be cleaned using, for example and without limitation, a cleaning solution made as follows. Prepare a phosphate buffer by mixing phosphate buffer powder (for example, phosphate buffer powder obtainable from Wako Pure Chemical of Osaka, Japan) with ultra-pure water until a 1/15M solution having a pH of 7.4 is achieved. Top surfaces 105, 206 and 305 of substrates 101, 201 and 302, respectively, may be cleaned by a method disclosed in an article by Sato et al. entitled "Integration of an Immunosorbant Assay System Analysis of Secretory Human Immunoglobulin A on Polystyrene Beads in a Microchip" in *Anal Chem.,* 72, 2000, pp. 1144-1147, which method comprises: (a) irrigating the top surfaces with the phosphate buffer solution; (b) then rinsing with ultra-pure and/or deionized water; and (c) then drying the surface.

It is useful to attach enough antibodies to the substrate per unit surface area of substrate to immobilize a target microorganism and/or chemical. There are several classes of antibodies: IgA, IgD, IgE, IgG, and IgM; and maximum adsorption of an IgG antibody onto a polymer has been observed to occur at pH 7. Thus, in accordance with one or more embodiments, and as disclosed in an article by Turkmen, et al. entitled "Phenylalanine Containing Hydrophobic Nanospheres for Antibody Purification" in *Biotechnol. Prog.*, 24, 2008, pp. 1297-1303, a liquid containing the antibody is maintained at a pH of about 6-8 during the adsorption process. In accordance with one or more embodiments that use a polymer substrate structure, a method for adsorbing antibodies onto such a polymer substrate structure, as disclosed in an article by Qian et al. entitled "Immobilization of Antibodies on Ultraflat Polystyrene Surfaces" in *Clinical Chemistry*, 46:9, 2000, pp. 1456-1463, comprises: (a) adding antibodies until they reach a concentration of 0.001-10 mg/mL to a coating buffer, for example, a 40-60 mmol/L carbonate buffer at about pH 9.0-10.5; (b) wetting the polymer substrate structure by immersion, rinsing or spraying with the antibody-buffer mixture; (c) incubating the wet polymer substrate structure for about 7-9 hours at about 1-10 degrees Celsius; (d) rinsing the polymer substrate structure with deionized water to remove excess antibody-buffer mixture; and (d) drying the polymer substrate structure with nitrogen. In accordance with one or more such embodiments, and as disclosed in an article by Boyd et al. entitled "Application of Antibody Adsorbed Polyester Cloth for Rapid Screening of Elution Conditions for Antigen Immunopurification" in *Immunological Investigations*, Volume 25, Issue 5&6, September 1996, pp. 447-453, the polymer substrate structure can be made of, for example and without limitation, polystyrene or polyester.

Antibody Adsorption onto Gold: Although, from a bonding strength standpoint, covalent linking of an antibody to a substrate structure is stronger than adsorbing the antibody onto a substrate structure, the inventor has discovered that, in accordance with one or more embodiments of the present invention, antibodies adsorbed onto a gold substrate provides bacterial immobilization—for example, see an article by Suo et al. entitled "Efficient Immobilization and Patterning of Live Bacterial Cells" in Langmuir 2008, 24, pp. 4161-4167 which describes a method for adsorption of antibodies on a gold substrate. Advantageously, this can simplify manufacturing processes by avoiding a need to covalently link antibodies to a gold substrate to fabricate immobilization particles.

Coating Substrate Support with Gold: In accordance with one or more embodiments of the present invention, a gold substrate is applied, for example, by deposition onto a substrate support, for example and without limitation, a polymer substrate support. Prior to applying the gold substrate, the substrate support may need to be cleaned. The substrate support may be cleaned with soap and water, and rinsed with water and/or by suitable cleaning methods described above. Alternatively, depending upon how clean the substrate support is after a prior manufacturing step, the substrate support can be cleaned using a glow discharge. If, as determined routinely by one of ordinary skill in the art, the substrate support is too dirty, the gold, or if necessary, a preceding chrome or titanium substrate layer, might not stick to the substrate support, thereby reducing the area for attachment of immobilization molecules. In accordance with one or more further embodiments, a substrate is comprised of several metal layers including, for example and without limitation, gold/titanium layers or gold/titanium/tungsten (for example, 20% titanium, 80% tungsten) layers, which titanium or titanium/tungsten layers have a thickness in a range from about 5 to about 100 Angstroms, and which titanium or titanium/tungsten layers are applied, for example, by deposition, to the substrate support prior to applying a gold layer. The titanium can be deposited using a process such as, for example and without limitation, a vacuum sputtering process, or any other deposition process capable of depositing such titanium or titanium/tungsten layers. In accordance with one or more embodiments, gold can be deposited using a vacuum sputtering process, and the gold substrate layer may have a thickness in a range from about 5 to about 200 Angstroms. If the gold substrate layer is too thin, it might not form a continuous layer, and instead, it will form islands of gold and voids in gold coverage that will provide a less effective bonding area for immobilization molecules. Although the gold substrate layer can be made thicker than 100 Angstroms, it may not be required to be thicker, and it will be less expensive to keep the gold substrate layer to a thickness of about 100 Angstroms.

In accordance with one or more further embodiments, to help promote adhesion of immobilization molecules to the substrate structure, a chromium substrate layer is deposited, for example and without limitation, vacuum deposited, to a thickness in a range from about 0.1 to about 5 nm on a substrate support, and this is followed by applying a gold substrate layer thereon having a thickness in a range from about 5 to about 100 nm.

Cleaning the Gold Surface: In accordance with one or more embodiments, the surface of a gold substrate may be cleaned using, for example and without limitation, the following method, wetting the gold substrate surface with a boiling solution of $H_2O_2$ (35%), $NH_3$ (25%) and Milli-Q water in a 1:1:5 ratio mixture for 10 minutes and by rinsing in Milli-Q water, which method is disclosed in an article by Schmid et al. entitled "Site-directed antibody immobilization on gold substrate for surface plasmon resonance sensors" in *Sensor and Actuators B: Chemical*, Vol. 113, Issue 1, 17 Jan. 2006, pp. 297-303 (the Schmid article").

Maintaining Gold Cleanliness: Once a gold substrate layer is deposited, its surface should be kept clean enough for successful adsorption of the immobilization molecules. The surface of the gold substrate layer can be kept clean using one or more of the following procedures to handle the substrate after deposition. Such procedures include, for example and without limitation, High Efficiency Particulate Absorbing (HEPA) filtration of air coming into contact with the gold substrate surface; transporting the gold substrates in a clean container; and ensuring that workers coming into close contact with the gold substrates wear clean room gowns, facemasks, eye protection, and so on. If the gold substrate surface becomes contaminated, it will require cleaning steps such as, for example and without limitation, one or more of the methods described above, soap and water, and/or glow discharge cleaning of the substrate material.

Covalent Linking Antibody to a Gold Substrate: In accordance with one or more embodiments, antibodies are covalently linked to a gold substrate that is attached to a polymer support substrate. A method for covalently linking antibodies to gold surfaces is disclosed, for example and without limitation, in an article by Siiman et al. entitled "Covalently Bound Antibody on Polystyrene Latex Beads: Formation, Stability, and Use in Analysis of White Blood Cell Populations" in *J. of Colloid and Interface Science*, 234, 2001, pp. 44-58, which article is incorporated by reference herein.

Covalently Linking an Antibody to a Gold Substrate Using a Thiol

In accordance with one or more embodiments, antibodies are covalently linked to a gold substrate. One method for attaching an antibody containing a thiol group to gold is to attach a thiol functional group contained in an antibody to the gold substrate. As is well known, a thiol functional group is an organic compound that contains a sulfur and hydrogen group (i.e., —SH). Suitable such methods for covalently linking antibodies to a gold substrate are disclosed in the following articles, which articles are incorporated by reference herein: an article by Karyakin et al. entitled "Oriented Immobilization of Antibodies onto the Gold Surfaces via Their Native Thiol Groups", in *Anal. Chem.*, 72(16), 2000, pp. 3805-3811; and the Schmid article.

Another method for attaching an antibody to a gold substrate comprises attaching a thiol-containing compound to the gold substrate, and then linking the antibody to the thiol-containing compound. A suitable thiol-containing compound is, for example and without limitation, dithiobis (succinimidyl undecanoate) ("DSU")—when DSU is chemisorbed onto a gold substrate, it induces amine reactive sites to be formed on the gold surface. In accordance with one or more such embodiments, a thiol such as, for example and without limitation, is attached to the substrate in a manner described below, and an aptamer or an antibody is attached to the thiol. One such method for covalently linking antibodies to a gold substrate is disclosed in an article by Mosher, et al. entitled "Microminiaturized Immunoassays Using Atomic Force Microscopy and Compositionally Patterned Antigen Arrays" in Anal. Chem., 70, 1998, pp. 1233-1241 (the "Mosher article") and comprises, for example and without limitation: (a) wetting top surfaces 105, 206 or 305 of gold substrates 101, 201 or 302, respectively, by immersion, rinsing or spraying with a dilute ethanolic solution of DSU (at a concentration in a range from about 0.1 to about 1.0 mM) for a length of time in a range from about 8 to about 24 hours; (b) adding antibodies (until they reach a concentration in a range from about 0.5 to about 2.0 mg/mL) to 50 mM of Dulbecco's phosphate buffer (PBS) (Dulbecco's PBS is available from Life Technologies accessible at www.lifetechnologies.com) having a pH in a range from about 5.5 to about 6.5; and (c) wetting gold top surfaces by immersion, rinsing, or spraying with the antibody-buffer mixture (for example, immersion in the antibody-buffer mixture for a length of time in a range from about 30 minutes to about 12 hours, where 90 minutes is normally sufficient).

Another method for covalently linking antibodies to a gold substrate is also disclosed in the Mosher article and comprises: (a) wetting top surfaces 105, 206 or 305 of gold substrates 101, 201 or 302, respectively, with a solution of dithiobissuccinimide propionate (DSP) in dimethysulfoxide (DMSO) (at a concentration in a range from about 0.00005M to about 0.00050M) at room temperature for a length of time in a range from about 1.5 to about 2.5 hours; (b) rinsing the substrate with DMSO; (c) rinsing the substrate with PBS having a pH in a range from about 6.9 to about 7.9 (in accordance with a method disclosed in the Schmid article); (d) adding antibodies (until they reach a concentration in a range from about 0.5 to about 2.0 mg/mL) to 50 mM of Dulbecco's PBS having a pH in a range from about 5.5 to about 6.5; (e) wetting gold surfaces by immersion, rinsing or spraying with the antibody-buffer mixture (for example, by immersion in the antibody-buffer mixture for a length of time in a range from about 30 minutes to about 12 hours where 90 minutes is normally sufficient).

Still another method for covalently linking antibodies to a gold substrate is also disclosed in the Mosher article, which method yields more antibodies having their Fc fragments attached to the gold substrate at a side opposite target microorganism or chemical binding fragments of the antibodies. Fc fragments are portions of an antibody that do not attach to antigens. The method comprises: (a) wetting top surfaces 105, 206 or 305 of gold substrates 101, 201 or 302, respectively, with a solution of DSP in DMSO (at a concentration in a range from about 0.0002M to about 0.0010M) at room temperature for a length of time in a range from about 1.5 to about 2.5 hours; (b) rinsing the substrate with DMSO; (c) rinsing the substrate with PBS having a pH in a range from about 6.9 to about 7.9; (d) covalently attaching a Protein A layer to a thiol linked gold substrate by soaking the gold substrate a length of time in a range from about 4 to about 10 hours at a temperature in a range from about 1 to about 8 degrees Celsius in a Protein A solution in a phosphate buffer (the solution having a concentration in a range from about 0.1 to about 4 mg/ml); (e) wetting the gold substrate with an ethanolamine hydrochloride solution having a concentration in a range from about 0.1 to about 3 M and having a pH in a range from about 7.6 to about 9.6 for a length of time in a range from about 0.1 to about 2 hours to block residual reacting sites; (f) washing the substrate with distilled water; (g) drying the substrate in accordance with a method disclosed in the Schmid article; (h) adding antibodies (until they reach a concentration in a range from about 0.5 to about 2.0 mg/mL) to about 40 to about 60 mM of Dulbecco's PBS having a pH in a range from about 5.5 to about 6.5; (i) wetting gold surfaces by immersion, rinsing or spraying with the antibody-buffer mixture (for example, by immersion in the antibody-buffer mixture for a length of time in a range from about 30 minutes to about 12 hours where 90 minutes is normally sufficient.

Covalently Linking an Antibody to a Gold Substrate Using Biotin and Streptavidin: In accordance with one or more embodiments, immobilization particles are made by depositing streptavidin on a gold substrate, attaching biotin to an antibody and/or antibody fragment and attaching the biotin-conjugated antibody and/or antibody fragment to the streptavidin, thereby forming a bond between the biotin and streptavidin.

A method for bonding antibodies to a gold surface using biotin and streptavidin is disclosed in an article by Kim et. al. entitled "Selective immobilization of proteins on gold dot arrays and characterization using chemical force microscopy" in *J. of Colloid and Interface Science*, 334, 2009, pp. 161-6, which article is incorporated by reference herein. In accordance with one or more such embodiments, octadecanethiol (ODT) may be applied to a gold substrate to prevent adhesion of antibodies, for example and without limitation, in areas of the substrate such as near and around edges, to prevent adhesion of antibodies.

Immobilization Particle with an Aptamer

It is believed that aptamers have several advantages over antibodies in fabricating immobilization particles in accordance with one or more embodiments of the present invention. For example, aptamers may be synthesized without using animals or other live organisms, and therefore, they may have minimal batch-to-batch variation, which batch-to-batch variation is typical of antibody manufacture. In addition, aptamers are non-toxic, relatively non-immunogenic, and they bind to whole cell or molecular targets with similar affinity and specificity as antibodies. In further addition, aptamers are small so they may be less susceptible to steric interference. In still further addition, aptamers can penetrate into a cell's interior for secure attachment. In yet still further addition, DNA aptamers are more thermally stable than antibodies. Lastly, aptamers are readily mass-produced and this makes them less expensive to use than antibodies.

Aptamer Selection: Once a target microorganism or molecule is identified and isolated, it is can be used to select an aptamer to fabricate one or more embodiments of the present invention. In accordance with one or more embodiments, aptamers are, for example and without limitation, one or more of the following: a DNA, an RNA and a peptide. In accordance with one or more embodiments, aptamers suitable for use in fabricating one or more embodiments include aptamers selected in accordance with one or more methods disclosed in the following articles (which articles are incorporated by reference herein): (a) an article by Tuerk, et al. entitled "Systematic evolution of ligands by exponential enrichment: RNA ligands to bacteriophage T4 DNA polymerase" in *Science,* 249, 3 Aug. 1990, pp. 505-510; (b) an article by Shamah et al. entitled "Complex Target SELEX" in Accounts of Chemical Research, Vol. 41. No 1., January 2008, pp. 130-138; (c) an article by Homann et al. entitled "Combinatorial selection of high affinity RNA ligands to live African trypanosomes" in *Nucleic Acids Research*, Vol. 27, No. 9, January 2008 pp. 2006-2014; (d) an article by Wang et al. entitled "In vitro selection of novel RNA ligands that bind human cytomegalovirus and block viral infection" in *RNA,* 6, 2000, pp. 571-583; (e) an article by Keefe et al. entitled "SELEX with modified nucleotides" in *Current Opinion in Chemical Biology,* 12, 2008, pp. 448-456; (f) an article by Hamula et al. entitled "Selection of Aptamers against Live Bacterial Cells" in *Anal. Chem.,* 80, 2008, pp. 7812-7819; and (g) an article by Hall et al. entitled "In Vitro Selection of RNA Aptamers to a Protein Target by Filter Immobilization" in *Current Protocols in Molecular Biology,* October 2009, pp. 24.3.1-24.3.27. As is well known to those of ordinary skill in the art, the SELEX process, the Complex Target SELEX process and the Counter SELEX process are selection processes that use a starting library of oligonucleotides and oligopeptides (approximately $10^5$) that contain randomized regions.

Aptamer Selection—Autoimmune Mimics: In accordance with one or more embodiments, aptamers are selected to immobilize one or more autoimmune mimics. Such autoimmune mimics include, for example and without limitation: (a) tryptophan peptide from myelin basic protein (see an article by Westall et al. entitled "Essential chemical requirements for induction of allergic encephalomyelitis" in *Nature,* 229, 1971 pp. 22-24); (b) mid-region from myelin basic protein (see an article by Shapira et al. entitled "Biological activity and synthesis of an encephalitogenic determinant" in *Science,* 172, 1971, pp. 736-738); (c) hyperacute site from myelin basic protein (see an article by Westall et al. entitled "Hyperacute autoimmune encephalomyelitis-unique determinant conferred by serine in a synthetic autoantigen" in *Nature,* 269, 1977 pp. 425-427); (d) S-antigen 375-386 (see an article by Dua et al. entitled "Structure-function studies of s-antigen: use of proteases to reveal a dominant uveitogenic site" in *Autoimmunity,* 10, 1991, pp. 153-163); (e) acetylcholine receptor 129-145 (see an article by Yoshikawa et al. entitled "A 17-mer self-peptide of acetylcholine receptor binds to B cell MHC class II, activates helper T cells, and stimulates autoantibody production and electrophysiologic signs of myasthenia gravis" in *J. Immunol.* 159, 1997, pp. 1570-1577); (f) acetylcholine receptor 67-75 (see an article by Bellone et al. entitled "The main region of the nicotinic acetylcholine receptor" in *J. Immunol.,* 143, 1989, pp. 3568-3579); (g) Sm b/B' protein proline region (see an article by James et al. entitled "Side-chain specificities and molecular modeling of peptide determinants for two anti-Sm B/B' autoantibodies" in *J. Autoimmunity,* 12, 1999, pp. 43-49); and (h) tropomyosin isomer V 4-10 (see an article by Vera et al. entitled "Tropmodulin-binding site mapped to residues 7-14 at the N-terminal heptad repeats of tropomyosin isoform 5" in *Arch. Biochem. Biophys,* 378, 2000, pp. 16-24). Suitable aptamers which immobilize the above-identified mimics are selected using any one of a number of methods that are well known to those of ordinary skill in the art routinely and without undue experimentation, for example and without limitation, using one of the SELEX type of processes.

Aptamer Selection—Immobilizing Bacteria, Fungi, Viruses, Serpins and Chemicals: In accordance with one or more embodiments, aptamers are selected to immobilize, for example and without limitation, one or more of the following genera of bacteria (use of such immobilization particles provides a method of treating or mitigating symptoms of diseases associated with such genera of bacteria): (a) for Multiple Sclerosis, the following genera of bacteria, *Enterococcus, Streptococcus, Lactobacillus, Bacteroides, Escherichia, Clostridium, Serratia, Bifidobacterium* and *Fusobacterium;* (b) for ulcerative colitis, the following genera of bacteria, *Burkholderia, Mycobacterium, Bacillus, Clostridium* and *Methylobacterium;* (c) for Lupus, the following genera of bacteria, *Burkholderia, Mycobacterium, Pseudomonas, Methylobacterium, Vibrio* and *Clostridium;* (d) for Uveoretinitis, the following genera of bacteria, *Bacteriodes, Bacillus, Clostridium, Lactobacillus, Fusobacterium, Vibrio, Ruminococcus* and *Methylococcus;* and (e) for rheumatoid arthritis, the following genera of bacteria, gram positive bacteria. It is believed that removing these genera of bacteria from a host is useful as they can exacerbate symptoms corresponding to the identified diseases. Suitable aptamers which immobilize the above-identified genera of bacteria are selected and manufactured using any one of a number of methods that are well known to those of ordinary skill in the art routinely and without undue experimentation, for example and without limitation, using one of the SELEX type of processes. Suitable aptamers which can serve as immobilization molecules to immobilize the above-identified genera of bacteria are readily commercially available, for example and without limitation, *Lactobacillium acidophilus* (hemag1P) is a suitable aptamer that is available from Aptagen, LLC. (accessible at http://www.aptagen.com).

In accordance with one or more embodiments, aptamers are selected to immobilize, for example and without limitation, one or more of the following genera of fungi: *Saccharomyces* and *Candida.* Suitable aptamers which immobilize the above-identified genera of fungi are selected and manufactured using any one of a number of methods that are well known to those of ordinary skill in the art routinely and without undue experimentation, for example and without limitation, using one of the SELEX type of processes.

In accordance with one or more embodiments, aptamers are selected to immobilize, for example and without limitation, one or more of the following viruses: Influenza, Herpes, and Cytomegalovirus. Suitable aptamers which immobilize the above-identified viruses are selected and manufactured using any one of a number of methods that are well known to those of ordinary skill in the art routinely and without undue experimentation, for example and without limitation, using one of the SELEX type of processes. Suitable aptamers which can serve as immobilization molecules to immobilize the above-identified genera of viruses are readily commercially available, for example and without limitation, Human Influenza A virus H3N2 (P30-10-16) is a suitable aptamer that is available from Aptagen, LLC. (accessible at http://www.aptagen.com).

In accordance with one or more embodiments, aptamers are to immobilize serpins—as is well known to those of ordinary skill in the art, serpins are a group of proteins that inhibit proteases. Suitable aptamers which immobilize the serpins are selected using any one of a number of methods that are well known to those of ordinary skill in the art routinely and without undue experimentation, for example and without limitation, using one of the SELEX type of processes.

In accordance with one or more embodiments, aptamers can be used to immobilize chemicals, such as but not limited to, the chemical theophylline—as is well known to those of ordinary skill in the art, theophylline is found in tea leaves. Suitable aptamers which can serve as immobilization molecules to immobilize the above-identified food chemical are readily commercially available, for example and without limitation, Anti-theophylline is a suitable aptamer that is available from GeneLink, Inc. (accessible at http://www-.genelink.com).

Aptamer Selection—pH Effects: The gastrointestinal tract has a large range of pH from approximately 1 to 8. In accordance with one or more embodiments of the present invention, when performing an aptamer selection process using the SELEX process, or its variants, a solution containing aptamers undergoing a selection process should be in the same range of pH that one would expect immobilization of the target microorganism or chemical to occur. For example, if a target microorganism were to be found in the small intestine, one ought to select an aptamer in a solution having a pH in a range from about 2 to about 6. If the target microorganism were to be found in the large intestine, one ought to select an aptamer in a solution having a pH in a range from about 6 to about 8.

Aptamer Adsorption onto Polymer: In accordance with one or more embodiments, aptamers are adsorbed onto a polymer substrate in accordance with suitable methods disclosed in the literature such as a method disclosed, for example and without limitation, in an article by Balamurugan et al. entitled "Surface Immobilization Methods for aptamer diagnostic applications" in *Analytical and Bioanalytical Chemistry*, vol. 390, issue no. 4, February 2008, which article is incorporated by reference herein.

Aptamer Adsorption onto Gold: In accordance with one or more embodiments, aptamers are adsorbed onto a gold substrate in accordance with suitable methods disclosed in the literature such as a method disclosed, for example and without limitation, in an article by Wang et al. entitled "Aptamer biosensor for protein detection using gold nanoparticles" in *Analytical Biochemistry*, vol. 373, issue no. 2 February 2008, which article is incorporated by reference herein.

Covalently Linking an Aptamer to a Gold Substrate: In accordance with one or more embodiments, aptamers are covalently linked onto a gold substrate in accordance with suitable methods disclosed in the literature such as a method disclosed, for example and without limitation, a method disclosed in an article by Saran et al. entitled "Micromechanical Detection of Proteins Using Aptamer-Based Receptor Molecules" in *Anal. Chem.*, 76, 2004, pp. 3194-3198 disclosing how an 5' etiolated aptamer is immobilized on gold, which article is incorporated by reference herein.

Covalently Linking an Aptamer to a Gold Substrate Using Biotin: In accordance with one or more embodiments, aptamers are covalently linked onto a gold substrate in accordance with suitable methods disclosed in the literature such as a method disclosed, for example and without limitation, a method disclosed in an article by Liss et al. entitled "An Aptamer-Based Quartz Crystal Protein Biosensor" in *Anal. Chem.*, 74, 2002, pp. 4488-4495 disclosing how 5' biotinylated aptamer is immobilized on streptavidin fixed on a gold surface with DSP, which article is incorporated by reference herein.

Fabricating Immobilization Particles Having Concavities in a Polymer Substrate/Polymer Substrate Support or Concavities in a Gold Substrate/Polymer Substrate Support:

Polymers are moldable/castable/injettable, and in accordance with one or more embodiments of the present invention, the immobilization particle comprises a substrate structure fabricated as (a) a molded/cast/inkjetted polymer substrate/polymer substrate support; or (b) a gold substrate/polymer substrate support. In accordance with one or more such embodiments, a mold is made from a silicon or ceramic wafer using standard manufacturing methods used to manufacture semiconductor circuits and MEMS. For example and without limitation, in accordance one or more such embodiments, a mold is made from a silicon wafer that is micromachined using semiconductor manufacturing equipment (other molding substrates may be used if non-wafer manufacturing equipment and processes are used). The method comprises the following: (a) spinning (or vapor phase depositing) and baking photoresist onto a top, polished surface of a silicon wafer (for example and without limitation, a wafer having a diameter in a range from about 4" to about 12"); (b) preparing a photo mask having a grid pattern; (c) exposing the photoresist-coated wafer (or other molding substrate) in a suitable stepper and developing the photoresist coating to expose the pattern; (d) dry or wet etching to a depth in a range of about 0.01 microns to about 500 microns (the depth is based on an aspect ratio of depth:feature width in a range from about 001:1 to about 5:1)—for dry etching, one may use a standard silicon wafer etcher such as an Applied Materials eMAX chamber, a Producer chamber, or a HART chamber with a standard dry etching process—which chambers are available from Applied Materials, Inc. of Santa Clara, Calif.; and for wet etching, one may use standard semiconductor techniques for wet etching silicon, quartz or other ceramic material wafers (if molding substrates other than silicon are used, one can use appropriate etching techniques that are well known to those of ordinary skill in the art to create a mold to make immobilization regions in the polymer substrate as well as patterned regions for spacers); (e) cleaning and drying the wafer or other molding substrate; (f) applying a release chemical according to manufacturer's specification to prevent a castable polymer from sticking to the etched wafer (any one of a number of suitable release chemicals are well known to those of ordinary skill in the art) (in accordance with one or more embodiments of the present invention, the castable polymer can be, for example and without limitation, polyurethane); (g) pouring and/or inkjetting the castable polymer onto the wafer or other molding substrate; (h) placing a sandwiching silicon wafer onto the cast polymer and applying an amount of pressure required to ensure uniform thickness of molded cavities (the amount of pressure can be determined by one of ordinary skill in the art routinely and without undue experimentation); (i) curing the castable polymer according to manufacturer's specification; (j) separating the silicon wafers from both sides of the cast polymer material; (k) cleaning the cast polymer to remove the release chemical (for example, the cleaning step can entail washing with semiconductor grade acetone followed by semiconductor grade isopropyl alcohol); (l) skip to step (n) if the substrate is not gold, sputtering gold and other required metal films as described above onto a side of the cast polymer material having cavities to a thickness in a range from about 40 to about 500 Angstroms (the deposition may use a sputtering tool that is well known to those of ordinary skill in the art such as, for example and without limitation, an Applied Materials Endura PVD chamber with a gold and/or other metal targets with any one of a number of sputtering process recipes that are well known to those of ordinary skill in the art—an Applied Materials Endura PVD chamber is available from Applied Materials, Inc.); (m) removing the wafer from the sputtering tool; (n) applying a protective film, such as, for example and without limitation, a pressure sensitive adhesive kapton film or a PTFE film onto the flat, cavity-less side of the cast polymer material; (o) if the substrate is gold, covalently linking antibodies to the gold substrate deposited on the cast polymer material substrate support as described above; (o') if the substrate is not gold, applying antibodies to the surface of the cast polymer material substrate as described above; (p) as an optional step to remove antibodies adsorbed outside the cavities, placing the cast polymer material, cavity-side down, onto a chemical mechanical planarization (CMP) pad of an Applied Materials Reflexion CMP machine for a time duration in a range from about 1 to about 100 seconds, using a platen speed in a range from about 10 to about 200 RPM, a head rotation speed in a range from about 10 to about 200 RPM, a head membrane pressure in a range from about 0.2 to about 20 PSI for each zone, and DI water with no slurry in an amount in a range from about 0.5 to about 10 liter/min (an Applied Materials Reflexion CMP machine is available from Applied Materials, Inc.); (q) removing the protective pressure sensitive adhesive film from the underside of the cast polymer material; (r) aligning the cast polymer material into a mounting support so that an excimer, infra-red or near infra-red laser can cut each cavity into individual immobilization particles, the laser power density being set to a range from about 10 to 1,000,000 mW/cm$^2$ and the linear feed rate being set to a range from about 0.1 to about 1000 cm/sec; and (s) laser cutting each immobilization particle and separate the particles. In accordance with one or more further embodiments, the immobilization particles can be cut by, for example and without limitation, a sharp cutting tool, an electrical discharge, thermally, a water saw, blasted abrasive materials, and any one of a number of other processes that are well known to those of ordinary skill in the art.

Immobilization Particles Having Antibodies and/or Aptamers Adsorbed onto a Porous Polymer Substrate and Polymer Spacers:

In accordance with one or more embodiments, an immobilization particle includes a substrate structure comprised of a substrate/substrate support which is comprised of a woven, porous polymer such as, for example and without limitation, polyester, polystyrene, polyurethane, nylon, fabric, paper or filter or a thin film such as, for example and without limitation, Mylar. In accordance with one or more such embodiments, the polymer material may be a sheet of the polymer fabric, paper, filter or thin film. For example, polyester films, such as Ultra-Polyester, are available in rolled films that are thicker than 1.5 microns—although the useful thickness is limited by handling concerns during manufacturing, thinner is better because there is more surface-to-volume area available. Making immobilization particles with higher surface-to-volume ratios is advantageous in that it enables a host, for example and without limitation, a mammal, to ingest smaller volumes of immobilization particles to immobilize target microorganism(s) and/or chemical(s). For full production, the sheet of polymer paper/film used to fabricate a substrate/substrate support can be on a roll which is manufactured in a continuous process using suitable processing equipment. In accordance with one or more embodiments, a method of making an immobilization particle comprises: (a) cleaning a paper/film/fabric polymer substrate in accordance with one or more of the methods for cleaning polymer described above; (b) adsorbing immobilization molecules (for example and without limitation, an aptamer and/or an antibody) onto a side of the polymer having concave features, such as: (i) concave features made using a mold; or (ii) concave features made by pressure using a die, or a polymer having surfaces created by voids in between fibers of a fabric; (c) fabricating spacers to prevent immobilized target microorganisms and/or chemicals from communicating with a host's tissue; and (d) cutting the polymer paper/film/fabric/filter substrate/substrate support (using one or more of the above-identified cutting methods) into pieces that are small enough to avoid digestive blockage if the immobilization particles are to be swallowed (if the immobilization particles are to be used as a dressing, they can be cut into larger pieces). In particular, a suitable immobilization particle can be in the form of: (a) a square having a side whose length is in a range from about 10 microns to about 5000 microns or (b) a circle having a diameter whose length is in a range from about 10 microns to about 5000 microns. If an immobilization particle is to be used as a dressing, the fabric, paper, filter or film polymer substrate can be cut in suitable larger pieces. Note, that in cutting a polymer paper/film/fabric/filter substrate/substrate support into pieces for GI use, the cutting action should destroy immobilization molecules disposed at, as well as any immobilization molecules disposed a small distance inbound from, the perimeter of the cuts to prevent immobilized targets from being disposed too close to an edge of the particle. In accordance with one or more such embodiments, the distance of a cut from the perimeter ought to be at least at large as the largest dimension of an intended immobilization target. Thus, for example, for a target bacterium having a largest dimension of 5 microns, immobilizing molecules need to be destroyed to a distance of about 5 microns from the perimeter.

In accordance with one or more embodiments, a method for fabricating spacers comprises the following steps. First, inkjetting and/or silkscreening features, for example and without limitation, dots, on one or both sides of a polymer paper/film/fabric/filter substrate/substrate support, wherein (a) the height of the features is in a range from about 1 micron to about 500 microns, i.e., a height which is taller than a sum of the longest dimension of the intended target microorganism and/or chemical and the longest dimension of the immobilization molecule; (b) the spacing between the features is in a range from about 1 micron to about 500 microns; and (c) a ratio between the diameter and height of the features is approximately 1:1 to prevent breakage. It should be understood that the features do not have to be circular, and in accordance with one or more embodiments, the features can have any suitable shape, as long as such features are tall enough and spaced closely enough together to prevent immobilized target microorganisms or chemicals from interacting with a host's tissue. In accordance with one or more such embodiments, the features can be made of the classes/types of materials mentioned above, such as, for example and without limitation, polymers. In addition, polymers such as polyurethane can be added to the substrate/substrate support by inkjetting.

The method of fabricating spacers further comprises heating the polymer substrate/substrate support (for example and without limitation, a polymer paper/film/fabric/filter) beyond its glass transition temperature to soften the polymer and to enable it to sag or get pushed into a form (if the substrate/substrate support sags into a form by gravity, the deformation process will not require a tool to push the material into the form). To heat the polymer substrate/support substrate, the material can be heated before a tool pushes the polymer substrate/support substrate into the form or a tool can provide the heat locally (for example and without limitation, upon contact) to the spacer. To keep the heated area local to the spacer, the heating process can take place in vacuum to prevent conductive heat transfer through the air. If a heated tool is used to push the substrate/support substrate, the heated tool may also be used to inactivate immobilization molecules by denaturing, hiding, or destroying them on and/or near the spacers upon contact. The step of inactivating assures that there is no host response when high points of spacer features come into contact with intestinal or other bodily tissue. If immobilization molecules are to be disposed on both sides of a substrate/substrate support, the high spots need to be pushed in and out, respectively, of the substrate/substrate support plane (like an egg carton) so that there are high spots on both sides of the substrate.

An alternative method of fabricating spacers comprises impacting the substrate/support substrate with a tool with enough force to form the substrate/support substrate. In accordance with one such method, the substrate does not have immobilization molecules attached prior to impacting. During impacting, sufficient force is applied to create concave dimples with adjacent raised high spots or embossments that inhibit a host's response when high spots of spacer features touch intestinal, or other bodily, tissue. The amount of force used may be determined by one of ordinary skill in the art routinely and without undue experimentation. Next, immobilization molecules are attached using one or more of the above-identified methods. Next, immobilization molecules are neutralized (for example and without limitation, inactivation or removal) at predetermined locations by, for example and without limitation, ion beam milling. In accordance with another such method, immobilization molecules are attached prior to impacting. To simultaneously neutralize (for example and without limitation, inactivate or remove) immobilization molecules at predetermined locations and create the spacers, sufficient force is applied to crush and inactivate immobilization molecules and to create concave dimples with adjacent raised high spots or embossments. The amount of force used may be determined by one of ordinary skill in the art routinely and without undue experimentation.

Immobilization Particles Having Antibodies and/or Aptamers Covalently Linked onto a Gold Substrate/Porous Polymer Substrate Support and Polymer Spacers:

In accordance with one or more embodiments, an immobilization particle comprises a gold substrate and substrate support comprised of a woven, porous polymer, such as, for example and without limitation, polyester, polystyrene, polyurethane, nylon, fabric, paper, filter or thin film such as, for example and without limitation, Mylar. In accordance with one or more such embodiments, the polymer material may be a sheet of the polymer fabric, paper, filter or thin film. For example, polyester films, such as Ultra-Polyester, are available in rolled films that are thicker than 1.5 microns—although the useful thickness is limited by handling concerns during manufacturing, thinner is better because there is more surface-to-volume area available. In accordance with one or more such embodiments, a method of making immobilization particles comprises: (a) cleaning a paper/film/fabric polymer substrate support in accordance with one or more of the methods for cleaning polymer described above; (b) sputtering gold and/or any other metal film in accordance with any one of such methods described above onto the side of the polymer having concave features, such as, but not limited to, dimples, blind holes, and spaces between fibers to a thickness in a range from about 40 to about 500 Angstroms, both sides of the porous polymer may be coated with metal if needed; (c) covalently linking antibodies to the gold substrate in accordance with one or more such methods described above; (d) fabricating polymer spacers to prevent immobilized microorganisms or chemicals from communicating with a host's tissues in accordance the methods described above; and (e) cutting the polymer paper/film/fabric/filter substrate/substrate support into pieces that are small enough to avoid digestive blockage if the immobilization particles are to be swallowed.

Immobilization Particles Having Antibodies and/or Aptamers Adsorbed onto Interior Surfaces of a Tube:

Some types immobilization particles, such as immobilization particle 700 described above in conjunction with FIG. 10, resemble a tube and have immobilization molecules attached to their interior surfaces. In accordance with one or more such embodiments, a substrate is extruded into a tube. Once the tube is drawn, a fluid containing immobilization molecules (for example a fluid having one or more of the above-described chemistries) is introduced into the hollow space of the tube to permit the immobilization molecules to become attached to the substrate. After the immobilization molecules become attached, the tube is cut using one or more of the above-described methods to appropriate lengths to create immobilization particles.

Alternative Method for Removing Immobilization Molecules Near Edges and Openings of Immobilization Particles:

As described above, it is desirable to remove immobilization molecules from regions of a substrate that may come in contact with a host's tissue. As described above, masking chemicals such as, for example and without limitation, ODT can be used to prevent adhesion of immobilization molecules. Alternatively, immobilization molecules can be selectively removed from a substrate by ion milling, excimer laser or by polishing.

Delivery Technology:

Since one use of immobilization particles fabricated in accordance with one or more embodiments of the present invention is to deliver the immobilization particles to a host's gastrointestinal tract, the immobilization particles can be delivered orally or via the anus. For oral delivery, a capsule, a tablet, a particle or a liquid form of delivery can be used. Depending upon the location of target microorganisms or chemicals, one can tailor the type of delivery method that is required.

pH Delivery: If the target delivery region is the large intestine, and the immobilization particles need to avoid deployment anywhere above the large intestine, one could encapsulate the immobilization particles inside a pH triggered capsule (the stomach's pH is approximately 1-2 (empty) and 3-4 (with food) due to stomach acid, and the pH of the gastrointestinal tract gradually increases along the small intestine until it reaches approximately 7 at the entrance of the large intestine). In accordance with one or more such embodiments, the immobilization particles are placed inside an open gel-cap, and then the gel-cap would be closed. Once closed, the gel-cap would be coated with a coating that dissolves when the pH of the environment reaches approximately 7. Examples of a suitable pH triggered coating include, for example and without limitation, pharmaceutical grade shellac or Eudragit-S polymer. A standard method of coating the capsules is to place the capsules in a rotating coating pan where the coating is sprayed onto the capsules while hot dry air is blown as the capsule tumbles inside the rotating coating pan.

Coatings: If the target delivery region is the small intestine, in accordance with one or more embodiments, the immobilization particles could be placed inside a gel-cap that would survive stomach acid and would dissolve upon entry into the small intestine. If the target delivery is a specific location in the small intestine, then a coating could be used for the gel-cal where the coating's triggering pH is tuned to open at the desired location in the small intestine. In accordance with one or more such embodiments, suitable coatings can be comprised of, for example and without limitation: (a) a pH sensitive poly(meth)acrylate copolymer such as, for example and without limitation, Eudragit FS, Eudragit S(-100), Eudragit RL, Eudragit RS(-100) or Eudragit L(-100); (b) ethylcellulose; (c) shellac; (d) deesterified pectin; (e) polygalacturonic acid (PGA or its potassium and sodium salts); (f) vinyl acetate resin; (g) carboxylated polyvinyl acetates; (h) polyvinyl/maleic anhydride copolymers; (i) ethylene/maleic anhydride copolymers; (j) methylacrylic acid/methyl methacrylate copolymers; (k) waxes; and (l) chitosan-calcium-alginate, as disclosed in: (i) an article by Sriamornsak et. al. entitled "Composite Film-Coated Tablets Intended for Colon-Specific Delivery of 5-Aminosalicylic Acid: Using Deesterified Pectin" in *Pharm Dev and Tech.*, Vol. 8, No. 3, 2003, pp. 311-318; (ii) an article by Hua et al. entitled "Technology to Obtain Sustained Release Characteristics of Drugs after Delivered to the Colon" in *J. of Drug Targeting*, Vol. 6, Issue 6, July 1999, pp. 439-448; (iii) an article by Rudolph et al. entitled "A new 5-ASA multi-unit dosage form for the therapy of ulcerative colitis" in *European J. of Pharmaceutics and Biopharmaceutics.*, Vol. 51, Issue 3, May 2001, pp. 183-190; (iv) an article by Gupta et al. entitled "A novel pH- and time-based multi-unit potential colonic drug delivery system. I. Development" in *International J. of Pharmaceutics*, Vol. 213, Issues 1-2, 1 Feb. 2001, pp. 83-91; and (iv) U.S. Pat. No. 5,401,512 entitled "Delayed release oral dosage forms for treatment of intestinal disorders."

Although many aptamers and antibodies can be stored as manufactured, some aptamers and antibodies may require an inert environment to protect them from oxygen or other sources of harm. In such case, an inert purge gas such as, for example and without limitation, nitrogen or argon can be used during manufacture of capsules. Also, a dry mixture of minerals and/or vitamins can be added to the immobilization particles. Examples of such minerals are, for example and without limitation, magnesium, selenium, manganese, iron, chromium, calcium, iodine, chloride, sodium, potassium, boron, bromide, silicon, phosphorus, titanium, rubidium, cobalt, copper, antimony, molybdenum, strontium, zinc, nickel, tungsten, scandium, vanadium, tellurium, tin, lanthanum, yttrium, silver, gallium, bismuth, zirconium, cerium, cesium, gold, beryllium, hafnium, samarium, terbium, europium, gadolinium, dysprosium, thorium, holmium, lutetium, erbium, ytterbium, neodymium, praseodymium, niobium, tantalum, thallium, rhenium, indium and so forth. These minerals can be added using a trace mineral powder complex manufactured by Trace Minerals Research of Ogden, Utah. The minerals can also be added individually or in mixtures by powders supplied by many nutritional supplement ingredient companies.

Packaging: In accordance with one or more embodiments, immobilization particles can be packaged into a sachet for storage and use and later ingested alone or with food. In accordance with one or more embodiments, immobilization particles can be delivered in a cap of a drink bottle where a patient breaks a seal and mixes the particles into the drink prior to consumption. In accordance with one or more embodiments, immobilization particles can be premixed in a liquid drink or foodstuff.

Coated Immobilization Particles: In accordance with one or more embodiments, an immobilization particle comprises enteric coatings, applied to individual immobilization particles or applied to a cluster of immobilization particles. Such immobilization particles can be ingested in a non-capsule or non-tablet form, and may be delivered to specific locations in the small intestine or in the large intestine. In accordance with one or more embodiments, enteric-coated immobilization particles can be packaged into a sachet for storage and later consumed alone or with food. In accordance with one or more embodiments, enteric-coated immobilization particles can be delivered in a cap of a drink bottle where a patient breaks a seal and mixes the immobilization particles into the drink prior to consumption. In accordance with one or more embodiments, enteric-coated immobilization particles can be premixed in a liquid drink or foodstuff. The coatings can be comprised of, for example and without limitation, (a) a pH sensitive poly(meth)acrylate copolymer such as, for example and without limitation, Eudragit FS, Eudragit S(-100), Eudragit RL, Eudragit RS(-100) and Eudragit L(-100); (b) ethylcellulose; (c) shellac; (d) deesterified pectin; (e) polygalacturonic acid ("PGA") or its potassium or sodium salts; (f) vinyl acetate resin; (g) carboxylated polyvinyl acetate; (h) polyvinyl/maleic anhydride copolymer; (i) ethylene/maleic anhydride copolymer; (j) methylacrylic acid/methyl methacrylate copolymer; (k) wax; and (l) chitosan-calcium-alginate, see an article by Sriamornsak et. al. entitled "Composite Film-Coated Tablets Intended for Colon-Specific Delivery of 5-Aminosalicylic Acid: Using Deesterified Pectin" in *Pharm Dev and Tech.*, Vol. 8, No. 3, 2003, pp. 311-318; an article by Hua et al. entitled "Technology to Obtain Sustained Release Characteristics of Drugs after Delivered to the Colon" in *J. of Drug Targeting*, Vol. 6, Issue 6, July 1999, pp. 439-448; an article by Rudolph et al. entitled "A new 5-ASA multi-unit dosage form for the therapy of ulcerative colitis" in *European J. of Pharmaceutics and Biopharmaceutics.*, Vol. 51, Issue 3, May 2001, pp. 183-190; an article by Gupta et al. entitled "A novel pH- and time-based multi-unit potential colonic drug delivery system. I. Development" in *International J. of Pharmaceutics*, Vol. 213, Issues 1-2, 1 Feb. 2001, pp. 83-91; and U.S. Pat. No. 5,401,512 entitled "Delayed release oral dosage forms for treatment of intestinal disorders." Since a patient can consume one or more embodiments of immobilization particles, in such form of delivery, a patient may think of the immobilization particles as a food product rather than a medical pill. Advantageously, this can have a psychological benefit that can improve patient compliance. In accordance with one or more embodiments, a flavored coating may be placed over the enteric coating to further disguise the medication as a food product and to further encourage compliance.

Liquid Delivery: In accordance with one or more embodiments, immobilization particles can be delivered in a mixture with a non-toxic liquid such as a food-based oil or water-based saline solution inside a sealed capsule. Appropriate preservative chemicals such as, for example and without limitation, antioxidants can be added to the liquid. Examples of suitable anti-oxidants that can be added include, for example and without limitation, vitamin C, vitamin E, alpha-lipoic acid, uric acid, selenium, a carotenoid, super oxide dismutase, resveratrol and pycnogenol.

Medicinal herbs can also be added to the liquid. Examples of suitable medicinal herbs that can be added include, for example and without limitation, aloe vera, Cat's Claw, Echinacea and Golden Seal. If an oil is used as a liquid, probiotics such as, for example and without limitation, *Lactobacillus* can be used in conjunction with and/or mixed with the immobilization particles.

Anal Delivery: In accordance with one or more embodiments, immobilization particles can be delivered via the anus in a suppository or enema form. The suppository can be a capsule containing immobilization particles. For an enema, the immobilization particles would be carried in a liquid. The immobilization particles and liquid can be stored in a plastic bottle until the enema need be ready for use. A nozzle on the plastic bottle would permit comfortable and safe delivery of the liquid and immobilization particles into the lower large intestine.

In accordance with one or more embodiments, various chemicals can be added to the enema to help treat an illness. Examples of suitable chemicals that can be added include, for example and without limitation, butyric acid, bismuth-containing compounds, alpha-lipoic acid, super oxide dismutase, Vitamin E, Vitamin C, Cat's Claw and aloe vera.

Topical Delivery: In accordance with one or more embodiments, immobilization particles can be applied topically to control infection or a microbiome on the skin, in the nasal and/or sinus cavity, in urogenital areas, in the ear and in the vaginal tract. In accordance with one or more such embodiments, the immobilization particles can be mixed into a topical cream or gel. In accordance with one or more further such embodiments, the immobilization particles can be mixed into an irrigation liquid or a gas.

In accordance with one or more embodiments, the immobilization particles can be embedded into a bandage to cover a wound or to control a microbiome locally.

Embodiments described above are exemplary. As such, many changes and modifications may be made to the description set forth above by those of ordinary skill in the art while remaining within the scope of the invention. In addition, materials, methods, and mechanisms suitable for fabricating embodiments have been described above by providing specific, non-limiting examples and/or by relying on the knowledge of one of ordinary skill in the art. Materials, methods, and mechanisms suitable for fabricating various embodiments or portions of various embodiments described above have not been repeated, for sake of brevity, wherever it should be well understood by those of ordinary skill in the art that the various embodiments or portions of the various embodiments could be fabricated utilizing the same or similar previously described materials, methods or mechanisms. As such, the scope of the invention should be determined with reference to the appended claims along with their full scope of equivalents.

What is claimed is:

1. A method for immobilizing a target microorganism found in a gastrointestinal tract of a mammal, the method comprising:
    introducing into the gastrointestinal tract of the mammal an immobilization particle comprising a flat substrate, one or more further structures disposed on both sides of the flat substrate, and immobilization molecules attached to one or more portions of one or more sides of the flat substrate and not to the one or more further structures, which immobilization molecules are capable of attaching to the target microorganism; and
    wherein the one or more further structures comprise columns having a height in a range from about 0.01 microns to about 500 microns and being spaced apart in a range from about 0.01 microns to about 500 microns.

2. The method of claim 1 further comprising removing the immobilization particles from the gastrointestinal tract.

3. The method of claim 2 wherein removing includes removing by administering an enema.

4. The method of claim 2 wherein removing the target microorganism entails removing the target microorganism without breaking the target microorganism into pieces.

5. The method of claim 1 wherein the one or more further structures inhibit contact between tissues of the gastrointestinal tract and/or dendritic cells attached to a wall of the gastrointestinal tract and the target microorganisms attached to the immobilization molecules.

6. The method of claim 1 wherein the immobilization particles are introduced into the gastrointestinal tract orally or via an anus of the mammal.

7. The method of claim 6 wherein the immobilization particles are introduced via the anus using a suppository comprised of a capsule containing the immobilization particles or an enema wherein the immobilization particles are carried in a liquid.

8. The method of claim 6 wherein the immobilization particles are introduced orally using a capsule, a tablet or a liquid.

9. The method of claim 6 wherein immobilization particles are orally delivered in a liquid mixture inside a sealed capsule.

10. The method of claim 9 wherein the liquid comprises a preservative and a food-based oil or a water-based saline solution.

11. The method of claim 6 wherein the immobilization particles are disposed inside a gel-cap which is coated with a substance that dissolves when the pH of the environment reaches about 7, whereby the immobilization particles are delivered orally into a large intestine without being deployed above the large intestine.

12. The method of claim 11 wherein the substance includes pharmaceutical grade shellac or a methylacrylic acid/methyl methacrylate copolymer.

13. The method of claim 6 wherein the immobilization particles are disposed inside a gel-cap that survives stomach acid and dissolves upon entry into the small intestine, whereby the immobilization particles are delivered orally into a small intestine.

14. The method of claim 6 wherein the immobilization particles are disposed inside a gel-cap that is coated with a substance that survives stomach acid and dissolves upon reaching a predetermined location in the small intestine.

15. The method of claim 1 wherein the immobilization molecules are one or more of antibodies or aptamers.

16. The method of claim 15 wherein one or more of the aptamers is a single-stranded RNA.

17. The method of claim 15 wherein the flat substrate is a gold substrate disposed on a polymer substrate support.

18. The method of claim 15 wherein the flat substrate is a polymer substrate.

* * * * *